US00RE33948E

United States Patent [19]

Schmidt et al.

[11] E Patent Number: Re. 33,948

[45] Reissued Date of Patent: Jun. 2, 1992

[54] β-LACTAM ANTIBIOTICS

[75] Inventors: Gunter Schmidt, Wuppertal; Hans-Joachim Zeiler, Velbert; Karl G. Metzger, Wuppertal, all of Fed. Rep. of Germany

[73] Assignee: Bayer Aktiengesellschaft, Leverkusen, Fed. Rep. of Germany

[21] Appl. No.: 400,200

[22] Filed: Aug. 29, 1989

Related U.S. Patent Documents

Reissue of:

[64] Patent No.: 4,748,163
Issued: May 31, 1988
Appl. No.: 832,483
Filed: Feb. 21, 1986

[30] Foreign Application Priority Data

Mar. 8, 1985 [DE] Fed. Rep. of Germany ..... 3508258

[51] Int. Cl.[5] ..... A61K 31/43; A61K 31/545; C07D 501/22; C07D 499/70

[52] U.S. Cl. ..... 514/194; 514/196; 514/201; 514/202; 514/203; 514/205; 514/206; 540/221; 540/222; 540/227; 540/228; 540/230; 540/328

[58] Field of Search ..... 514/194, 196, 201, 202, 514/203, 205, 206; 540/221, 222, 227, 228, 230, 328

[56] References Cited

U.S. PATENT DOCUMENTS

| | | | |
|---|---|---|---|
| 3,080,356 | 3/1963 | Catlin et al. | 540/328 |
| 4,317,775 | 3/1982 | Burri et al. | 540/328 |
| 4,395,412 | 7/1983 | Saikawa et al. | 540/230 X |
| 4,461,767 | 7/1984 | Breuer et al. | 514/202 |
| 4,496,560 | 1/1985 | Farge et al. | 514/204 |
| 4,537,886 | 8/1985 | Taylor et al. | 514/193 |

FOREIGN PATENT DOCUMENTS

| | | |
|---|---|---|
| 2408698 | 9/1974 | Fed. Rep. of Germany . |
| 2728578 | 1/1978 | Fed. Rep. of Germany . |
| 938321 | 3/1962 | United Kingdom . |
| 1174335 | 12/1969 | United Kingdom . |

*Primary Examiner*—Jose G. Dees
*Assistant Examiner*—Vera C. Clarke
*Attorney, Agent, or Firm*—Sprung Horn Kramer & Woods

[57] ABSTRACT

Antibacterially active and animal growth-promoting novel β-lactam compounds of the formula in which $R^1$ represents the radical Y representing N or $CR^9$, or Y—$R^7$ representing Z representing O, S, or $NR^{10}$, and $R^2$ represents hydrogen or a protective group.

23 Claims, No Drawings

β-LACTAM ANTIBIOTICS

Matter enclosed in heavy brackets [ ] appears in the original patent but forms no part of this reissue specification; matter printed in italics indicates the additions made by reissue.

The invention relates to β-lactam antibiotics, to processes for their preparation and to their use as and in medicaments, in particular as antibacterial, orally effective antibiotics.

It has been disclosed that various representatives of the 7-α-aminoacylcephalosporins with a variety of substituents in the 3-position of the molecule have antibiotic actions, thus for example cephalexin [7-(D-α-phenylglycylamido)-3-methyl-3-cephem-4-carboxylic acid], cefaclor [7-(D-α-phenylglycylamido)-3-chloro-3-cephem-4-carboxylic acid] (compare British Pat. No. 1,174,335; German Offenlegungsschrift (German Published Specification) Nos. 2,408,698 and 2,728,578).

Furthermore, a number of antibiotically effective α-aminopenicillanic acids has been disclosed, for example ampicillin (British Patent Specification No. 938.321) and amoxicillin (British Patent Specification No. 1.339.605).

The present invention relates to β-lactam compounds of the general formula I

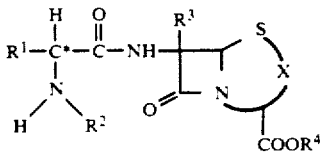

(I)

in which

X represents a radical of the formula

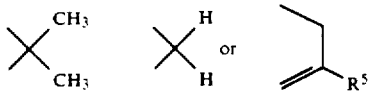

in which $R^5$ represents hydrogen, represents halogen, azido or represents straight-chain, branched or cyclic, saturated or unsaturated alkyl which has up to 7 C atoms and which is optionally substituted by halogen, $C_1$-$C_5$-hydroxy, $C_1$-$C_5$-alkylthio, —O-$CONH_2$, $C_2$-$C_{10}$-acyloxy, by a pyridinium radical which can be substituted once or several times, or by a radical of the formula

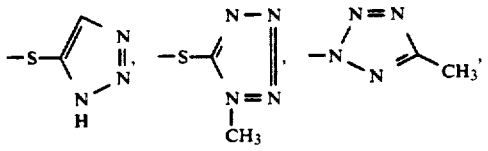

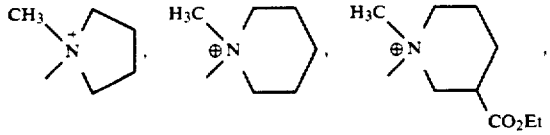

-continued

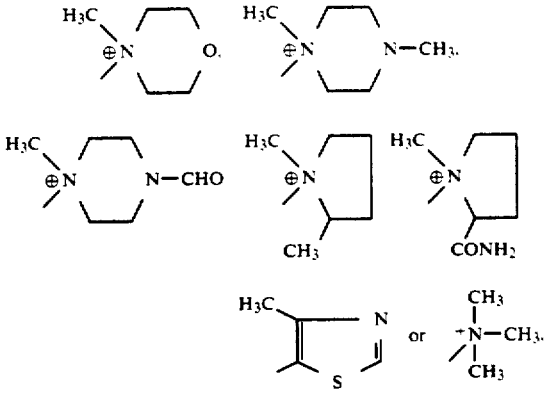

or represents $C_1$-$C_5$-alkoxy or $C_1$-$C_5$-alkylthio, $R^1$ represents the radical

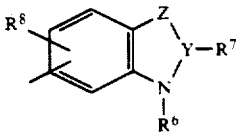

Y represents N or $CR^9$, or Y—$R^7$ representing >C=O or >C=N—$R^7$,

Z representing O, S or $NR^{10}$, $R^6$ representing hydrogen, representing hydroxyl or amino, or representing straight-chain, branched or cyclic, saturated or unsaturated alkyl which has up to 10 C atoms and is optionally substituted by halogen, optionally substituted amino, hydroxyl, cyano or $C_6$-$C_{10}$-aryl, or representing optionally substituted $C_6$-$C_{10}$-aryl, $R^7$ representing hydrogen, representing straight-chain, branched or cyclic, saturated or unsaturated alkyl which has up to 10 C atoms and which is optionally substituted by halogen, hydroxyl, alkoxy or alkoxycarbonyl, each having 1 to 6 C atoms, cyano, carboxyl, optionally substituted aryl, $SO_3H$ or by an optionally substituted amino group, or representing optionally substituted aryl, or $R^6$ and $R^7$ together completing a double bond, $R^8$ representing hydrogen, representing alkyl, alkoxy, alkylthio, each having 1 to 8 C atoms, representing trifluoromethyl or trifluoromethoxy, representing hydroxyl, mercapto, nitro or cyano, representing halogen, or representing an optionally substituted amino group, $R^9$ having the same meaning as $R^7$ and, additionally, representing halogen, representing $C_1$-$C_8$-alkoxy or $C_1$-$C_8$-alkylthio, representing an optionally substituted amino group, representing $SO_2$—$C_1$-$C_8$-alkyl or —$PO(OH)_2$, representing $SO_3H$ or $SO_2NH_2$, representing SH, OH, S-phenyl or O-phenyl, representing guanidino, amidino, —$NHNH_2$ or NHOH, representing optionally substituted heterocyclyl, or representing O-heterocyclyl or S-heterocyclyl, $R^{10}$ having the same meaning as $R^6$ but not completing a double bond with $R^7$, or $R^9$ and $R^{10}$ together representing a $C_2$–$C_4$-methylene chain which is optionally interrupted by oxgen or sulphur, $R^2$ represents hydrogen or represents an amino-protective group, $R^3$ represents hydrogen, represents alkoxy or alkylthio, each having up to 5 C atoms, represents an optionally substituted amino group, or represents NHCHO, and $R^4$ represents hydrogen, represents a carboxyl protective group, represents $—CH_2—O—CO—C(CH_3)_3$, represents $—CH_2—O—CO—CH_3$ or $—CH(CH_3)—O—CO—O—C_2H_5$, represents the radical of the formula

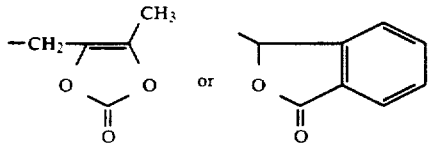

or represents alkali metal or ammonium ions.

Preferred compounds of the formula I are those in which

X represents a radical of the formula

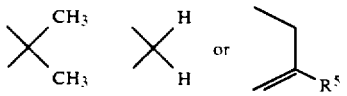

in which $R^5$ represents hydrogen, represents fluorine, chlorine or bromine, represents straight-chain or branched, saturated or unsatuated alkyl which has up to 5 C atoms and which is optionally substituted by one or more fluorine, chlorine, bromine, alkoxy or alkylthio each having 1 to 3 C atoms, carbamoyloxy, acetyloxy or benzoyloxy radicals or by a radical of the formula

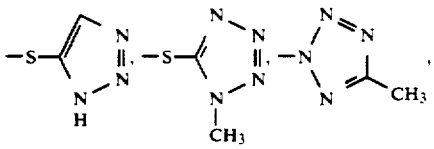

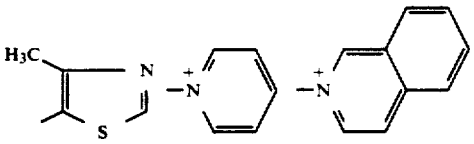

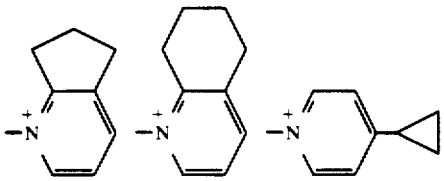

-continued

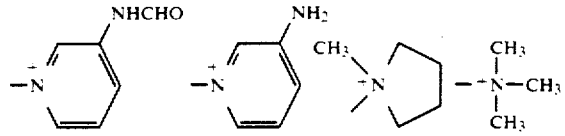

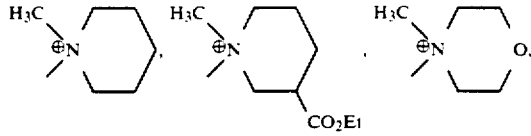

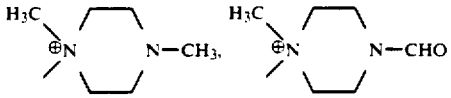

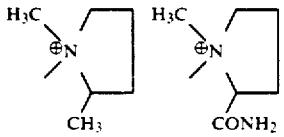

or represents $C_1$–$C_3$-alkoxy or $C_1$–$C_3$-alkylthio, $R^1$ represents a radical of the formula

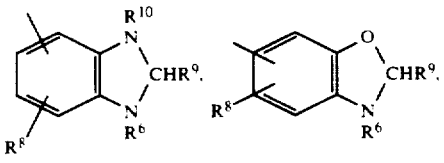

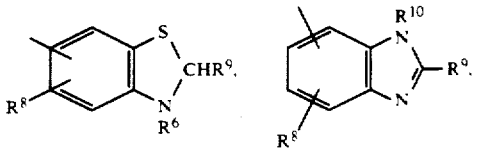

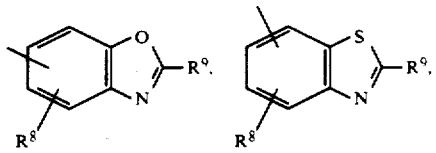

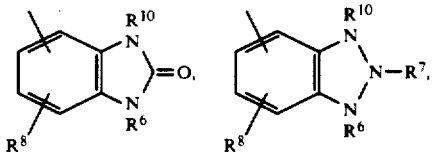

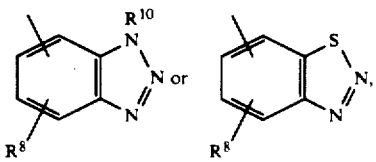

$R^6$ representing hydrogen, representing hydroxyl or amino, or representing straight-chain, branched or cyclic, saturated or unsaturated alkyl which has up to 8 C atoms and which is optionally substituted by one or more of fluorine, chlorine, bromine, optionally substituted amino, hydroxyl or phenyl, or representing optionally substituted aryl, $R^7$ representing hydrogen, or representing straight-chain, branched or cyclic, saturated or unsaturated alkyl which has up to 8 C atoms and which is optionally substituted by one or more of fluorine, chlorine, bromine, $C_1$-$C_4$-alkoxy, hydroxyl, carboxyl, phenyl, $SO_3H$ or an optionally substituted amino group, or representing optionally substituted aryl, $R^8$ representing hydrogen, representing alkyl, alkoxy or alkylthio, each having 1 to 6 C atoms, representing trifluoromethyl or trifluoromethoxy, representing hydroxyl, mercapto, nitro or cyano, representing fluorine, chlorine or bromine, or representing an optionally substituted amino group, $R^9$ having the same meaning as $R^7$ and, additionally, representing fluorine, chlorine or bromine, representing $C_1$-$C_6$-alkoxy or $C_1$-$C_6$-alkylthio, representing an optionally substituted amino group, representing $—SO_2—C_1$-$C_6$-alkyl or $—PO(OH)_2$, representing $—SO_3H$ or $—SO_2NH_2$, representing SH, OH, S-phenyl or O-phenyl, representing guanidino, $—NHNH_2$ or —NHOH, representing optionally substituted heterocyclyl or representing O-heterocyclyl or S-heterocyclyl, $R^{10}$ having the same meaning as $R^6$ but not completing a double bond with $R^7$, or $R^9$ and $R^{10}$ together representing a $C_2$-$C_4$-methylene chain which is optionally interrupted by sulphur, $R^2$ represents hydrogen or represents an amino-protective group, $R^3$ represents hydrogen, represents alkoxy or alkylthio, each having 1 to 3 C atoms, represents an optionally substituted amino group, or represents NHCHO, and $R^4$ represents hydrogen, represents a carboxyl protective group, represents $—CH_2—O—CO—C(CH_3)_3$, represents $—CH(CH_3)—O—CO—O—C_2H_5$ or $—CH_2—O—CO—CH_3$, represents the radical of the formula

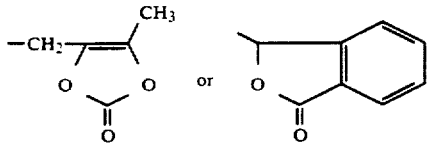

or represents $Na^+$, $Li^+$, $K^+$ or $NH_4^+$.

In the above definition, optionally substituted aryl represents phenyl which is substituted, identically or differently, once to three times, preferably once or twice, suitable substituents being alkyl, alkylthio or alkoxy, each having 1 to 4, preferably 1 or 2 C atoms, halogen, preferably fluorine, chlorine or bromine, nitro, cyano, hydroxyl, amino, trifluoromethyl, trifluoromethylthio or trifluoromethoxy.

In the definition, an optionally substituted amino group represents the group

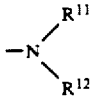

$R^{11}$ and $R^{12}$ being identical or different and representing hydrogen, representing aryl, preferably phenyl, representing $C_1$-$C_8$-alkyl, preferably $C_1$-$C_5$-alkyl, representing $C_7$-$C_{14}$-aralkyl, preferably benzyl, or representing $C_2$-$C_{10}$-acyl, preferably acetyl or benzoyl.

When $R^2$ represents an amino-protective group, then it preferably represents an amino-protective group which can be readily eliminated, such as, for example, tert.-butoxycarbonyl (Boc), trityl (Trt), benzyloxycarbonyl (Z), formyl, chloroacetyl or 1-methyl-2-ethoxycarbonylvinyl.

When $R^4$ is a carboxyl-protective group then it is preferably a protective group which is customary in $\beta$-lactam chemistry, preferably tert.-butyl, decyl, 2,2,2-trichloroethyl, benzyl, 4-methoxybenzyl, 4-nitrobenzyl, triphenylmethyl or diphenylmethyl, acetoxymethyl, allyl or trimethylsilyl.

The term heterocyclyl represents saturated and unsaturated heterocycles having one to four nitrogen and/or oxygen and/or sulphur atoms, and preferably represents pyrrolyl, pyrrolidinyl, pyrazolyl, imidazolyl, pyridyl, pyridazinyl, pyrimidyl, pyrazinyl, quinolyl, isoquinolyl, indolyl, quinoxalyl, quinazolyl, piperidinyl, morpholinyl, piperazinyl, thiomorpholinyl, furyl, thienyl, oxazolyl, thiazolyl, isoxazolyl, thiadiazolyl, triazolyl or tetrazolyl.

If the heterocycles are substituted, then they are substituted once to three times, preferably once or twice, identically or differently, by alkyl, alkylthio or alkoxy, each having 1 to 4, preferably 1 or 2 C atoms, halogen (preferably fluorine, chlorine or bromine), nitro, cyano, hydroxyl, amino, trifluoromethyl, trifluoromethoxy or trifluoromethylthio.

Particularly preferred compounds of the general formula I are those in which

X represents a radical of the formula

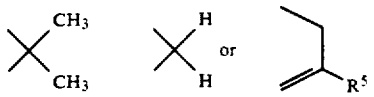

in which $R^5$ represents hydrogen, represents chlorine or fluorine, represents methyl, methoxy or methylthio, represents trifluoromethyl, vinyl, cis-propenyl, 3-chloro-1-propenyl, 3-iodo-1-propenyl, 3-pyridinio-1-propenyl, 3-(1-methyl-pyrrolidino)-1-propenyl 3-(1H-1,2,3-triazol-5-yl)-thio-1-propenyl, 3-(4-methylthiazol-5-yl)-1-propenyl or methoxymethyl, represents carbamoyloxymethyl, represents acetyloxymethyl or represents a radical of the formula

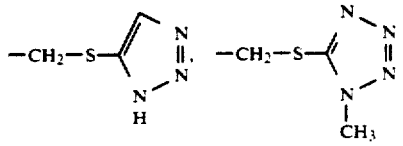

-continued

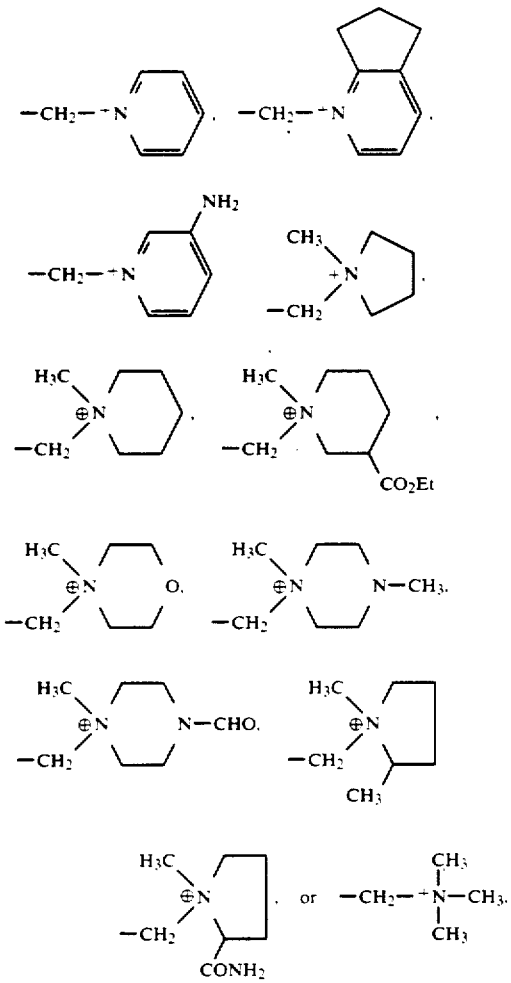

$R^1$ represents a radical of the formula

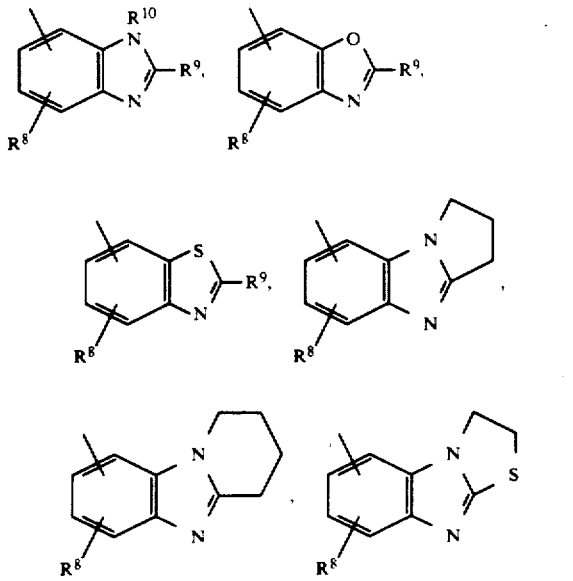

-continued

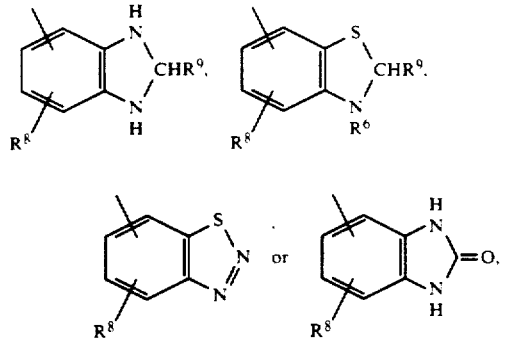

$R^6$ representing hydrogen, representing straight-chain, branched or cyclic, saturated or unsaturated alkyl (up to $C_6$) which is optionally substituted by one or more fluorine, amino, hydroxyl or phenyl, or representing optionally substituted aryl, $R^8$ representing hydrogen, representing alkyl, alkoxy or alkylthio, each having 1 to 4 C atoms, representing trifluoromethyl or trifluoromethoxy, representing hydroxyl, nitro or cyano, representing fluorine or chlorine, or representing amino, phenylamino, dimethylamino or acetylamino, $R^9$ representing hydrogen or representing straight-chain, branched or cyclic, saturated or unsaturated alkyl which has up to 6 C atoms and which is optionally substituted by one or more of fluorine, chlorine, $C_1$-$C_2$-alkoxy, hydroxyl, carboxyl, phenyl, $SO_3H$, amino, $C_1$-$C_3$-alkylamino, dialkylamino each of which has 1 to 3 C atoms, phenylamino, benzylamino or acetylamino, or representing fluorine, chlorine or bromine, representing $C_1$-$C_4$-alkoxy or $C_1$-$C_4$-alkylthio, representing optionally substituted aryl, representing amino, $C_1$-$C_3$-alkylamino or dialkylamino, each having 1 to 3 C atoms, phenylamino, benzylamino or acetylamino, representing $—SO_2—C_1$-$C_4$-alkyl, representing $SO_3H$ or $SO_2NH_2$, representing OH, SH, O-phenyl or S-phenyl, representing guanidino, $—NHNH_2$ or —NHOH or representing pyrrolyl, pyrrolidinyl, pyrazolyl, imidazolyl, pyridyl, quinolyl, isoquinolyl, furyl, thienyl, morpholinyl, piperidinyl, piperazinyl or pyrimidyl, each of which can optionally be substituted by fluorine, chlorine, methyl, nitro, cyano, hydroxyl, trifluoromethyl, methoxy or amino, or representing S-pyridyl or O-pyridyl, $R^{10}$ having the same meaning as $R^6$, $R^2$ represents hydrogen, or represents an amino-protective group, $R^3$ represents hydrogen, represents methoxy or methylthio, represents amino, $C_1$-$C_3$-alkylamino, dialkylamino each having 1 to 3 C atoms, phenylamino, benzylamino or acetylamino or represents NHCHO, and $R^4$ represents hydrogen, represents a carboxyl protective group, represents $—CH_2—O—CO—C(CH_3)_3$, represents $—CH(CH_3)—O—CO—O—C_2H_5$, represents a radical of the formula

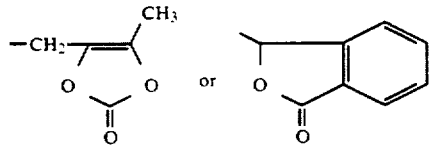

or represents $Li^+$, $Na^+$, $K^+$ or $NH_4^+$.

The terms amino-protective group and carboxyl-protective group have the meaning already indicated above.

The compounds of the formula I can be in the form of free acids, of esters, of internal salts or of non-toxic pharmaceutically tolerated salts of the acidic carboxyl groups, such as sodium, potassium, magnesium, calcium, aluminium or ammonium salts and non-toxic substituted ammonium salts, with amines such as di- or tri-lower alkylamines, procaine, dibenzylamine, N,N'-dibenzylethylenediamine, N-benzyl-β-phenylethylamine, N-methylmorpholine and N-ethylmorpholine, 1-ephenamine, dehydroabietylamine, N,N'-bis-dehydroabietylethylenediamine, N-lower alkylpiperidine and other amines which can be used for the formation of salts of penicillins and cephalosporins.

Because of the presence of the asymmetric carbon atom designated by *, the new β-lactam antibiotics of the formula I include the D-, L- and D,L-forms. The D-forms of the compounds of the general formula I, according to the invention, are preferred.

Both the mixtures of diastereomers and the D-form and L-form of the compounds according to the invention can be used for the treatment of bacterial infectious diseases. The compounds of the general formula I are obtained when compounds of the general formula IIa

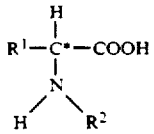

(IIa)

in which $R^1$ has the abovementioned meaning and in which $R^2$ represents an amino-protective group, are, after activation of the carboxyl group by conversion into a mixed anhydride, for example with pivaloyl chloride, ethyl or isobutyl chloroformate, after conversion into the mesylate using methanesulphonyl chloride or after conversion into an activated ester, for example with 1-hydroxybenzotriazole and dicyclohexylcarbodiimide, induced to react with compounds of the general formula III

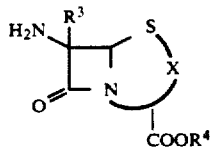

(III)

in which $R^3$, $R^4$ and X have the abovementioned meaning, then, where appropriate, protective groups are eliminated and the desired salts are prepared or the free acids are prepared from salts.

It is possible to use for the coupling of the aminoacids of the formula II with β-lactams of the formula III a large number of methods known from cephalosporin and penicillin chemistry.

It has proved to be advantageous to activate aminoacids of the general formula II and then to couple them with β-lactams of the general formula III, which are induced to dissolve as salts with an amine.

Activation with pivaloyl chloride or sulphonic acid derivatives of the formula IV, to give anhydrides of the formula Va and Vb, is particularly advantageous.

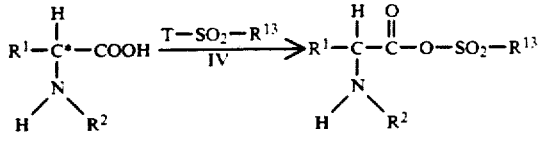

IIa Va or

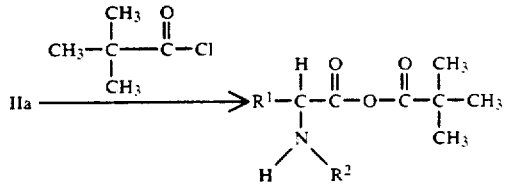

Vb in which $R^1$ has the abovementioned meaning, $R^2$ represents an amino-protective group, T represents a radical $R^{13}$—$SO_2$—O or halogen, and $R^{13}$ represents $C_1$–$C_{10}$-alkyl which is optionally substituted by fluorine, chlorine, cyano, phenyl, $C_1$–$C_4$-alkyl, $C_1$–$C_4$-alkoxy or $C_1$–$C_4$-alkylthio, or represents phenyl which is optionally substituted by fluorine, chlorine, bromine, cyano, $C_1$–$C_4$-alkyl, $C_1$–$C_4$-alkoxy, $C_1$–$C_4$-alkylthio, $C_1$–$C_4$-alkylcarbonyl, nitro or trifluoromethyl.

When $R^{13}$ is substituted, then preferably 1–3 substituents are present, preferably those mentioned.

$R^{13}$ very particularly preferably represents a methyl or p-tolyl radical.

The mixed anhydrides of the formula Va are prepared by dissolving the acids of the formula II and 1 to 1.4 equivalents of an amine in a solvent and allowing them to react with 1 to 1.2 equivalents of a sulphonic acid derivative of the formula IV.

Suitable solvents are all solvents which are stable under the reaction conditions, such as, for example, diethyl ether, tetrahydrofuran, acetonitrile, acetone, methylene chloride, chloroform or dimethylformamide.

Tertiary amines are suitable as the amine, such as, for example, triethylamine or tributylamine, as well as sterically hindered secondary amines such as, for example, diisopropylamine.

The reactions can be carried out at temperatures between −80° C. and room temperature, preferably between −60° C. and 0° C. The activation with Cl-$SO_2$-$CH_3$ is preferably carried out in dimethylformamide at −40° C. to −60° C. within 0.2 to 24 hours, preferably 0.5 to 5 hours.

It is possible to use for the dissolution of the compounds of the formula III the solvents mentioned for the preparation of the compounds of the formula V, and to use as the base the amines mentioned there.

It is also particularly advantageous to activate the acids of the general formula II by conversion into an activated ester with, for example, N-hydroxysuccinimide and dicyclohexylcarbodiimide or 1-hydroxybenzotriazole and dicyclohexylcarbodiimide.

Suitable solvents are all solvents which are also suitable for the preparation of anhydrides of the formula V.

The reactions can be carried out at temperatures between −30° C. and +100° C. Activation is advantageously carried out with 1-hydroxybenzotriazole and dicyclohexylcarbodiimide in dimethylformamide at room temperature for 2 to 6 hours, then the precipitated dicyclohexylurea is filtered off with suction, and reaction with a compound of the formula III, in the form of a solution of its amine salt, is carried out within 2 to 24 hours. It is possible to use for the dissolution of the compounds of the formula III the solvents mentioned for the preparation of the compounds of the formula V, and to use as the base the amines mentioned there.

Literature for amino and carboxyl protection and carbooxyl activation: M. Bodanszky, Principles of Peptide Synthesis, published by Springer, 1984. E. Gross, J. Meienhofer, The Peptides Vol. 2, Academic Press, 1980.

The stereochemically homogeneous D- or L-forms of the compounds of the formula I, according to the invention, are obtained when the mixtures of diastereomers are separated on, for example, HPLC columns from Merck, Dupont or Whatman.

On the other hand, the pure D- or L-form (preferably the D-form) is obtained when, even at the stage of the racemic aminoacid of the formula II, a chemical racemate resolution, for example with dehydroabietylamine, phenylethylamine or camphorsulphonic acid, or a racemate resolution via, for example, N-acetylamino acid derivatives, for example with subtilisin, penicillin acylase or pig kidney acylase, is carried out and then the stereochemically homogeneous D- and L-forms of the compounds of the formula II are reacted in the manner indicated.

Only some of the compounds of the general formula II are known. The compounds of the formula II can be synthesized by processes known from the literature, as shown in Scheme 1, the compounds of the formula VI representing the most important key compounds for the new amino acids of the formula II.

Scheme 1

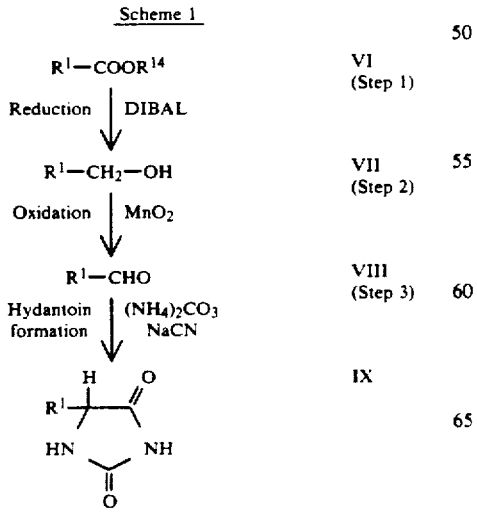

-continued

Scheme 1

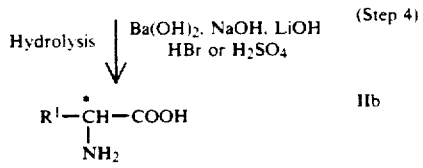

$R^1$ has the abovementioned meaning, $R^{14}$ represents $C_1$–$C_4$-alkyl.

The reduction of esters with diisobutylaluminum hydride (DIBAL) and sodium bis(2-methoxyethoxy)aluminum hydride (Red-Al) to give alcohols (step 1) is described in the literature: E. Winterfeld, Synthesis 1975, 617; A. E .G. Miller et al., J. Org. chem. 24, 627 (1959). The oxidation of primary alcohols with manganese(IV) oxide or pyridinium chromate to give aldehydes (step 2) is known in the literature: Methoden der Organischen Chemie (Methods of Organic Chemistry), Houben-Weyl, Vol. 4/1b; G. Piancatelli et al., Synthesis 1982, 245.

The new amino acids of the formula IIb are obtained when the aldehydes are reacted with sodium cyanide and ammonium carbonate by processes known from the literature [E. Ware, Chemical Reviews 46, 403 (1950)] (step 3) and then hydrolyzed with 10% strength sodium hydroxide solution, 48% strength hydrobromic acid, barium hydroxide or lithium hydroxide solution (step 4).

In the text which follows, the preparation of some new amino acids of the general formula II and of their precursors is described by way of example, $R^9$–$R^{14}$ having the abovementioned meaning:

(1) Benzothiazolylglycines:

The starting material for the synthesis of substituted benzothiazolylglycine derivatives is o-, m- or p-aminobenzoic ester. Benzothiazolecarboxylic acid derivatives are prepared by, for example, the synthetic scheme which follows:

Scheme 2

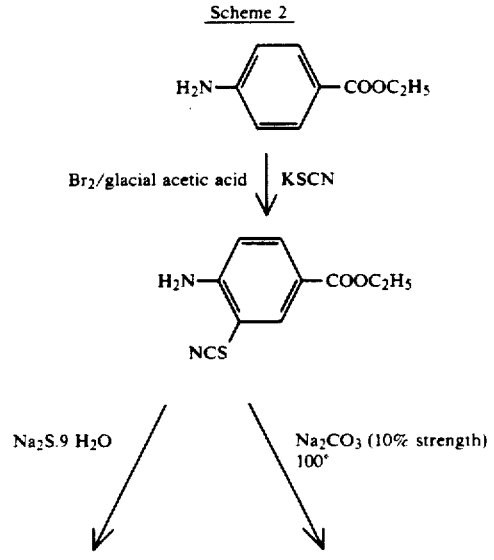

-continued

Scheme 2

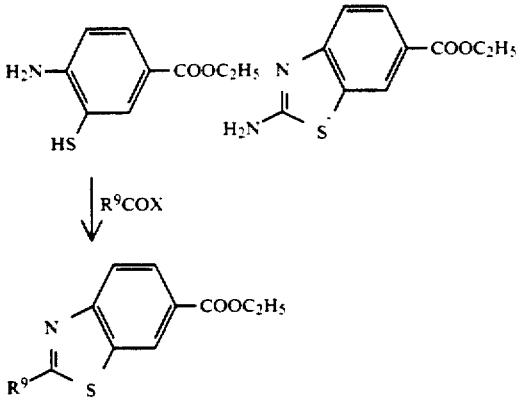

Literature: J. L. Wood, Substitution and Addition Reactions of Thiocyanogen, Organic Reactions, Vol. III, 240 (1946); M. T. Bogert et al., J. Am. Chem. Soc. 47, 3078 (1925); M. T. Bogert, J. Am. chem. soc. 57, 1529 (1935); J. M. Spraque et al., Thiazoles and Benzothiazoles, Heterocyclic Compounds, Vol. 5, 484 (1957), J. Wiley & Sons. The starting material for the synthesis of substituted benzothiazolylglycine derivatives is α-amino-α-(p-aminophenyl)acetic methyl ester:

Scheme 3

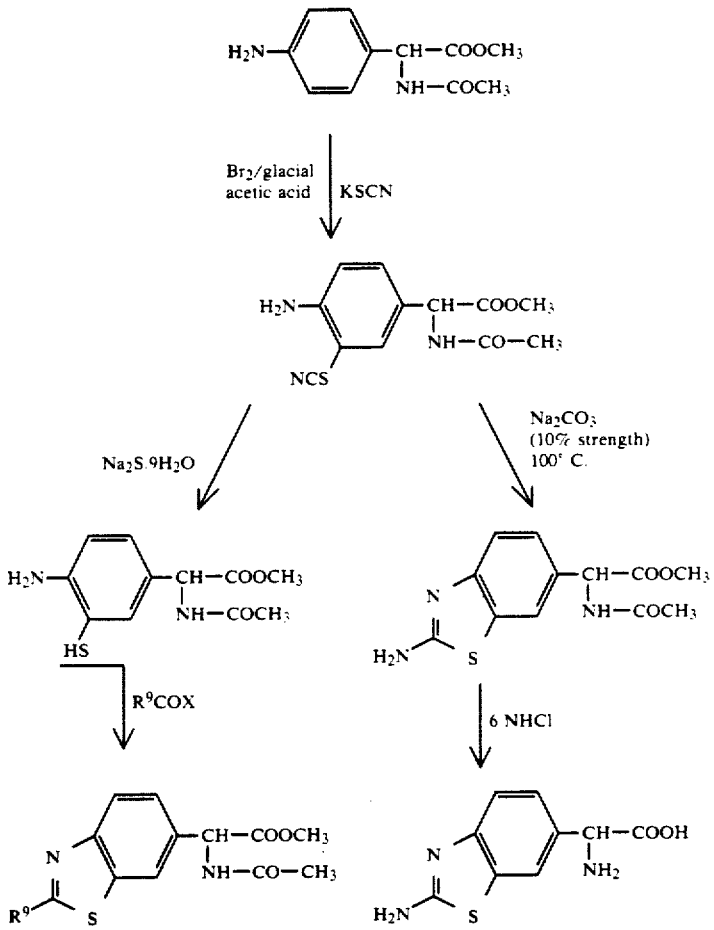

(2) Benzimidazolylglycines

Starting material for the synthesis of substituted benzimidazolylglycine derivatives is, for example, 3,4-diaminobenzoic acid. The substituted benzimidazolecarboxylic esters are prepared, for example, by the following synthetic scheme:

Scheme 4

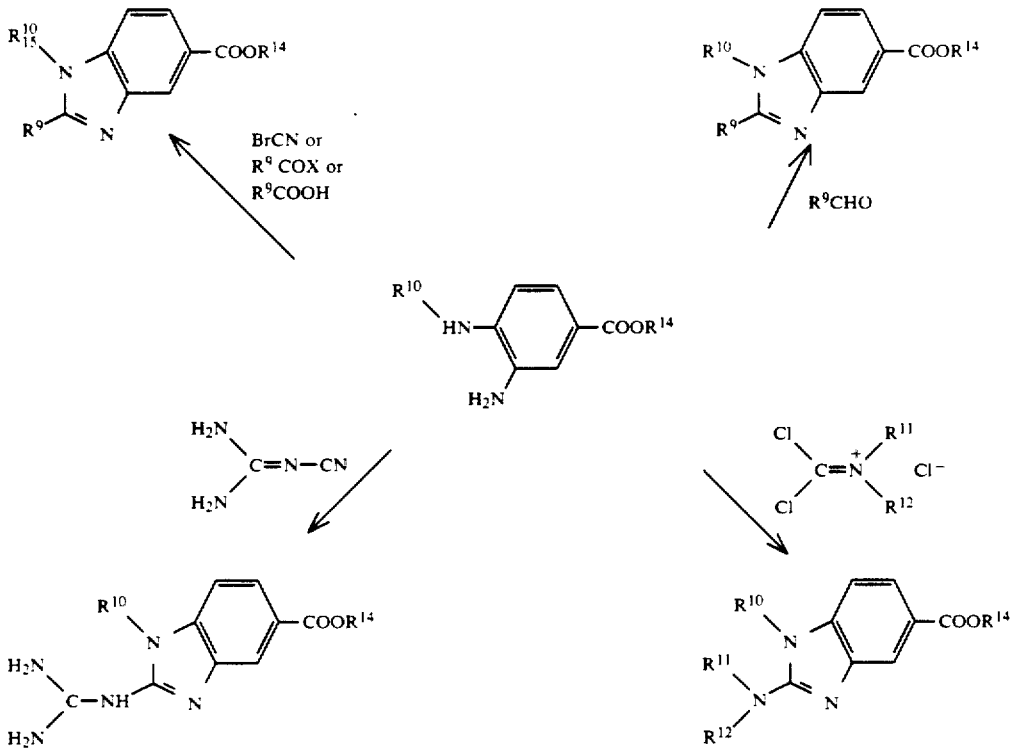

Literature: P. N. Preston, Chemical Reviews 74, 279 (1974); R. Rastogi et al., Synthesis 1983, 861; P. N. Preston, Benzimidazoles and Congeneric Tricyclic Compounds, Heterocyclic Compounds, Vol. 40, I and II, J. Wiley & Sons (1980, 1981).

(3) Benzoxazolylglycines

The starting material used for the synthesis of substituted benzoxazolylglycine derivatives is 3-amino-4-hydroxybenzoic acid, 3-hydroxy-4-aminobenzoic acid and D-α-amino-(3-amino-4-hydroxyphenyl)acetic acid methyl esters. The anellated phenylglycine derivatives and substituted benzoxazolecarboxylic acid derivatives are prepared by, for example, the following synthetic scheme:

Scheme 5:

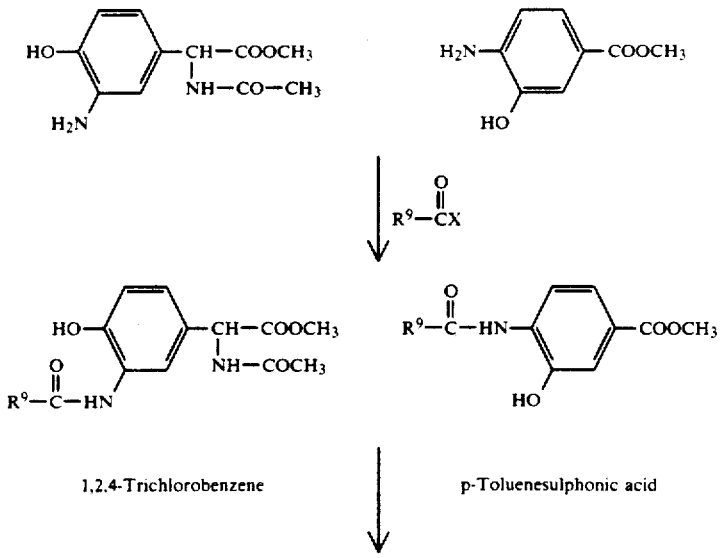

Scheme 5:

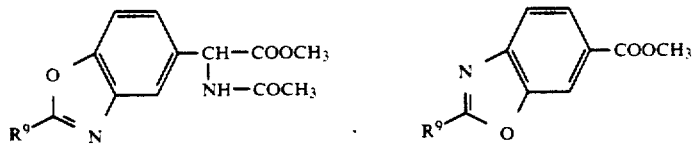

Literature: J. W. Cornforth, Benzoxazoles and Related Systems, Heterocyclic Compounds, Vol. 5, 418, J. Wiley & Sons (1957); R. Lakham et al., Advances in Oxazole Chemistry, Advances in Heterocyclic Chemistry, Vol. 17, 99, Academic Press (1974).

(4) Benzotriazolylglycines and benzothiadiazolylglycines 3,4-Diaminobenzoic acid and ethyl p-aminobenzoate are used as starting material for the synthesis of substituted benzotriazolylglycines and benzothiadiazolylglycines. The new benzo-condensed carboxylic acids and esters are prepared by, for example, the following synthetic scheme:

Scheme 6

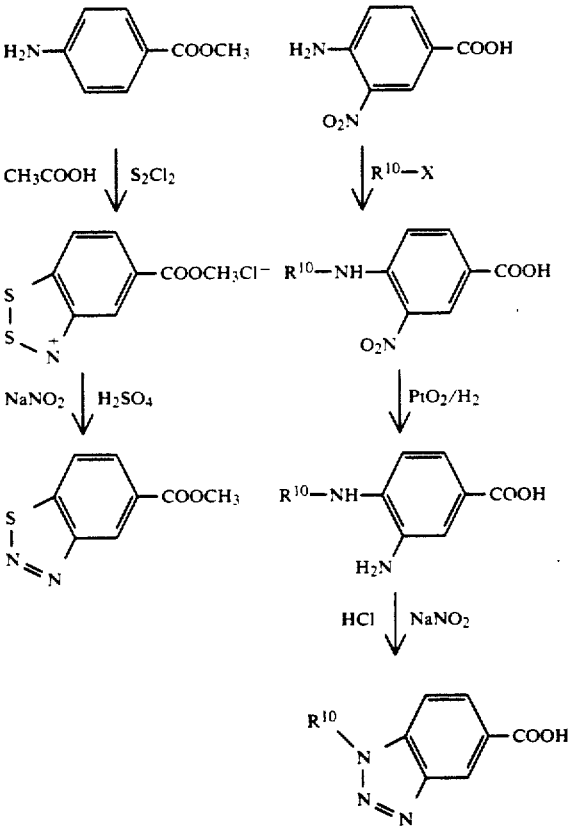

Literature: J. B. Carr, J. Heterocyclic Chem. 9, 1149 (1972)

The following parent substances of penicillins and cephalosporins, of the formula III, are used for the preparation of the compounds of the formula I according to the invention. ($R^3$, $R^4$ and $R^5$ have the abovementioned meaning).

(1) Cephalosporin parent substances (IIIa)

The cephalosporin parent substances used, derivatives from 7-amino-3-methyl-3-cephem-4-carboxylic acid (7-ADCA), 7-amino-3-chloro-3-cephem-4-carboxylic acid (7-ACCA) and 7-amino-3-methoxy-3-cephem-4-carboxylic acid, which are described in J. Med. Chem. 12, 310 (C. W. Ryan et al., 1969), U.S. Pat. No. 3,994,884, and German Offenlegungsschrift No. 2.606.196 are represented by the formulae below:

-continued (IIIa)

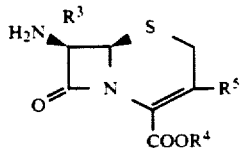

| $R^3$ | $R^4$ | $R^5$ |
|---|---|---|
| H | H | $CH_3$ |
| H | t-Butyl | $CH_3$ |
| H | H | Cl |
| H | 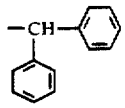 | Cl |
| H | H | H |
| $CH_3O$ | Trimethylsilyl | Br |
| H | Allyl | $OCH_3$ |
| $NH-\overset{O}{\overset{\|\|}{C}}-H$ | H | Cl |
| $NH-\overset{O}{\overset{\|\|}{C}}-H$ | t-Butyl | $CH_3$ |
| $CH_3S$ | t-Butyl | $CH_3$ |
| H | H (or Benzhydryl) | $CH=CH_2$ |
| H | H (or Benzhydryl) | $CH=CH-CH_3$ (cis) |

(2) Penicillin parent substances (IIIb)

In addition to 6-aminopenicillic acid and its typical modifications, 6-β-aminobisnorpenicillic acid (British Pat. No. 1,546,622) and 6-α-formamidopenicillin (P. H. Milner et al., J. Chem. Soc. Chem. Commun., 1984, 1335) are used for the preparation of the new compounds of the formula I:

IIIb

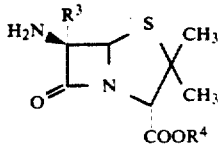

| $R^3$ | $R^4$ |
|---|---|
| H | H |

-continued

IIIb

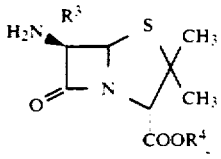

| $R^3$ | $R^4$ |
|---|---|
| H | $-CH_2O-CO-C(CH_3)_3$ |
| H | $-CH(CH_3)-OCOO-CH_2-CH_3$ |
| H | 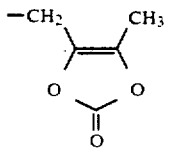 |
| $OCH_3$ | Allyl |
| $SCH_3$ | Trimethylsilyl |
| $NH-C(=O)-H$ | H |

Very particularly preferred compounds of the formula I, according to the invention, are listed in the preparation examples and in the tables which follow:

(a) Cephalosporins (Tables 1 and 2)

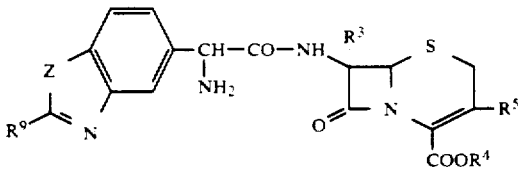

Z = NH, O, S

TABLE 1

| $R^3$ | $R^4$ | $R^5$ | $R^9$ |
|---|---|---|---|
| H | H | Cl | 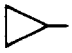 |
| H | H | $CH_3$ | 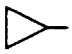 |
| H | H | $OCH_3$ | 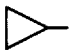 |
| H | H | Cl | $H_2N-C(=NH)-NH-$ |
| H | H | $OCH_3$ | $H_2N-C(=NH)-NH-$ |
| H | H | $CH_3$ | $H_2N-C(=NH)-NH-$ |
| H | H | $OCH_3$ | $H_2N-C(=NH)-NH-$ |
| H | H | $-CH=CH_2$ | $H_2N-C(=NH)-NH-$ |
| $NH-C(=O)-H$ | Na | Cl | $(CH_3)_2N-$ |
| H | H | $OCH_3$ | $(CH_3)_2N-$ |
| H | H | $CH_3$ | $(CH_3)_2N-$ |
| H | H | $-CH=CH_2$ | $(CH_3)_2N-$ |
| $NH-C(=O)-H$ | H | Cl | 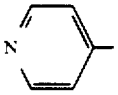 |
| H | t-Butyl | $OCH_3$ | 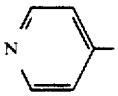 |
| H | H | $CH_3$ | 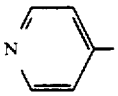 |
| H | H | $S-CH_3$ | 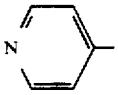 |
| H | Allyl | Cl | 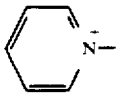 |
| H | H | Cl | 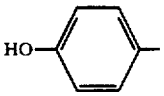 |
| H | H | $OCH_3$ | 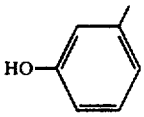 |
| H | H | $-CH=CH_2$ | 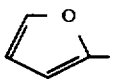 |
| $NH-C(=O)-H$ | H | Cl | 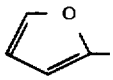 |

TABLE 1-continued

| $R^3$ | $R^4$ | $R^5$ | $R^9$ |
|---|---|---|---|
| H | H | $OCH_3$ | 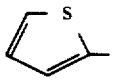 |
| H | H | Cl | $(CH_3)_2CH-$ |
| H | H | Cl | 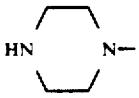 |
| H | H | $OCH_3$ | $H_2N-CH_2-$ |
| H | H | Cl | $H_2N-CH(CH_3)-$ |
| H | H | $CH_3$ | $CH_3O-CH_2-$ |
| H | H | Cl | 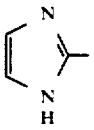 |
| H | H | $OCH_3$ | 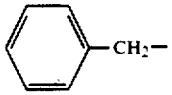 |
| H | H | Cl | $CH_3S-$ |
| H | H | $CH_3$ | 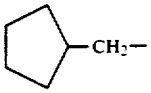 |
| H | H | Cl | 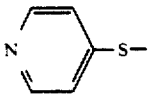 |

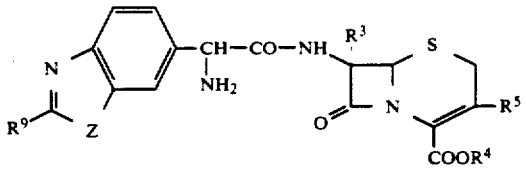

Z = S, O

TABLE 2

| $R^3$ | $R^4$ | $R^5$ | $R^9$ |
|---|---|---|---|
| H | H | Cl | $CH_3$ |
| $-NH-C(=O)-H$ | H | Cl | $CH_3$ |
| $OCH_3$ | Allyl- | $CH_3$ | $CH_3$ |
| H | H | Cl | H |
| H | H | $OCH_3$ | H |
| H | H | Cl | $H_2N-$ |

TABLE 2-continued

| $R^3$ | $R^4$ | $R^5$ | $R^9$ |
|---|---|---|---|
| H | H | Cl | 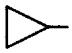 |
| $-NH-C(=O)-H$ | H | $CH_3$ | 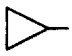 |
| H | H | $OCH_3$ | 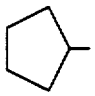 |
| H | Benzhydryl | $CH_3$ | 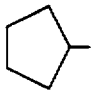 |
| H | H | Cl | 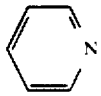 |
| H | H | Cl | 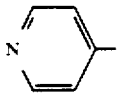 |
| H | H | $OCH_3$ | 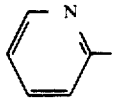 |
| H | H | $CH=CH_2$ | 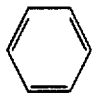 |
| H | H | Cl | 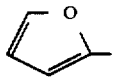 |
| H | H | $CH_3$ | 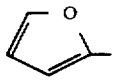 |
| H | H | Cl | 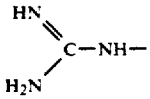 |
| H | H | Cl | $(CH_3)_2CH-$ |
| H | H | $CH_3$ | $(CH_3)_2CH-$ |
| H | Benzhydryl | $CH_3$ | $CH_3NH-$ |
| H | H | Cl | $HO-$ |
| H | H | $CH_3$ | $CH_3S-$ |
| H | H | Cl | $CH_3-SO_2-$ |
| H | H | $-CH=CH_2$ | $HO_3S-$ |
| H | H | Cl | $HO_3S$ |

(b) Penicillins (Tables 3 and 4)

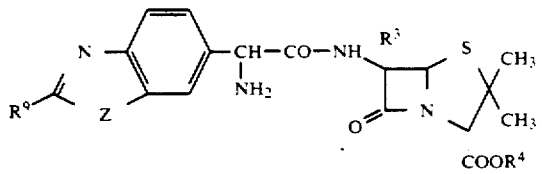
Z = NH, S, O
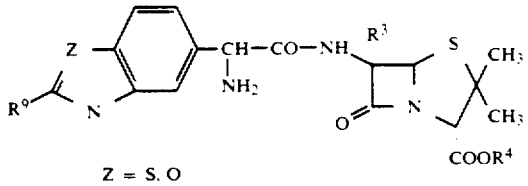
Z = S, O
TABLE 4
| $R^3$ | $R^4$ | $R^9$ |
|---|---|---|
| H | H | H |
TABLE 3
| $R^3$ | $R^4$ | $R^9$ |
|---|---|---|
| H | H | H |
| $NH-\overset{O}{\overset{\|\|}{C}}-H$ | H | $CH_3-$ |
| H | $-\underset{CH_3}{\underset{\|}{CH}}-O-CO-O-CH_2-CH_3$ | $CH_3-$ |
| H | $OCH_3$ | 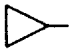 |
| H | 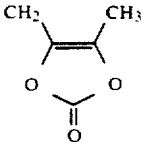 | 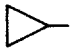 |
| H | H | 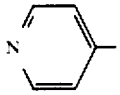 |
| H | H | 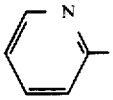 |
| H | H | 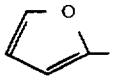 |
| $OCH_3$ | H | 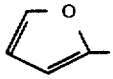 |
| H | H | 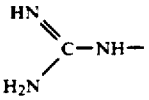 |
| H | H | 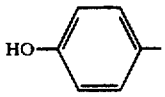 |
| H | H | 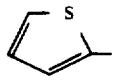 |

TABLE 4-continued

| $R^3$ | $R^4$ | $R^0$ |
|---|---|---|
| $NH-\overset{O}{\overset{\|\|}{C}}-H$ | H | $CH_3-$ |
| H | $-\underset{CH_3}{\underset{\|}{CH}}-O-CO-O-C_2H_5$ | $CH_3-$ |
| H | $OCH_3$ | 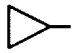 |
| H | 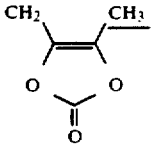 | 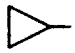 |
| H | H | 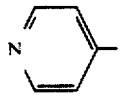 |
| H | H | 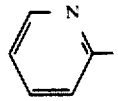 |
| H | H | 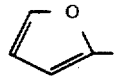 |
| $OCH_3$ | H | 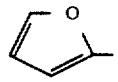 |
| H | H | 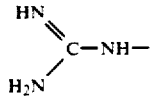 |

TABLE 4-continued

| $R^3$ | $R^4$ | $R^0$ |
|---|---|---|
| H | H | 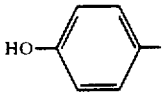 |
| H | H | 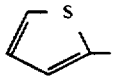 |

The compounds of the formula I, according to the invention, have low toxicity and a broad antibacterial spectrum for Gram-positive and Gram-negative organisms, in particular for Staphylococci, Streptococci, Enterococci and Haemophilus influenzae.

On parenteral or, in particular, oral administration, the new compounds are very active against microorganisms such as Staphylococci, for example Staph. aureus, Staph. epidermidis; Streptococci such as, for example, Streptococcus pyogenes, Streptococcus faecalis, Enterobacteriaceae, Escherichia coli, Klebsiella, Salmonella, Shigella and Proteus, for example Proteus mirabilis.

These properties make it possible to use them as chemotherapeutic active compounds in human and veterinary medicine.

In the table which follows, the minimum inhibitory concentrations (MIC values, μg/ml) for the compounds of the formula I, according to the invention, which are listed there are compared with that of cefaclor [M. Gorman et al., Cefaclor, Chronicles of Drug Discovery, Vol. 2, 49, J. Wiley & Sons (1983)]. The MIC values are determined by the agar dilution test using a multipoint inoculator, inspection being carried out after incubation at 37° C. for 18 to 24 hours. The growth medium used is Isosensitest agar.

| | Examples | | | | | | | |
|---|---|---|---|---|---|---|---|---|
| Organisms | 2a | 8 | 12a | 15a | 20 | 22 | 23 | Cefaclor |
| *E. coli* T 7 | 32 | 4 | 4 | 128 | 16 | 16 | 128 | 8 |
| *E. coli* A 261 | 8 | 2 | 2 | 8 | 4 | 4 | 8 | 2 |
| *E. coli* Neum. | 8 | 1 | 2 | 8 | 4 | 2 | 4 | 2 |
| *E. coli* 183/58 | >128 | >128 | >128 | >128 | >128 | >128 | >256 | >128 |
| *E. coli* F 14 | 128 | 32 | 128 | >128 | 128 | >128 | 256 | 16 |
| *E. coli* C 165 | 4 | 0.5 | 2 | 8 | 2 | 4 | 32 | 1 |
| *E. coli* 4322 | 4 | 0.5 | 16 | 8 | 2 | 4 | 4 | 1 |
| Klebs. 57 USA | 32 | 4 | 4 | 64 | 16 | 16 | 32 | 8 |
| Klebs. 63 | 1 | 0.5 | 1 | 8 | 2 | 1 | 2 | 1 |
| Klebs 1852 | 128 | 8 | 8 | 128 | 64 | 64 | 128 | 8 |
| Klebs. 6097 | 2 | 0.5 | 1 | 16 | 2 | 2 | 2 | 2 |
| Serratia 16001 | >128 | >128 | >128 | >128 | >128 | >128 | >256 | >128 |
| Serratia 16002 | >128 | >128 | >128 | >128 | >128 | >128 | >256 | >128 |
| Provid. 12012 | >128 | 32 | 32 | >128 | >128 | 128 | >256 | 32 |
| *Prot. morg.* 932 | >128 | >128 | >128 | >128 | >128 | >128 | 32 | >128 |
| *Prot. vulg.* 9023 | 128 | 64 | >128 | 128 | >128 | 128 | >256 | 64 |
| *Prot. vulg.* 1017 | >128 | >128 | >128 | >128 | >128 | >128 | 128 | >128 |
| *Prot. vulg.* N 6 | >128 | >128 | >128 | >128 | >128 | >128 | 4 | >128 |
| *Prot. rettg.* 10007 | >128 | >128 | >128 | >128 | >128 | >128 | >256 | >128 |
| *Prot. mir* 1235 | 1 | 2 | 4 | 8 | 8 | 2 | 4 | 4 |
| Staph. 1756 | 128 | 128 | 128 | >128 | 128 | 128 | >256 | >128 |
| Staph. 133 | 0.5 | 0.5 | 2 | 4 | 2 | 1 | 1 | 2 |
| Staph. 25022 | 0.5 | 0.5 | 2 | 4 | 4 | 1 | 2 | 4 |
| Staph. 25470 | 128 | 64 | >128 | >128 | 128 | >128 | >256 | >128 |
| Staph. E 25185 | 0.06 | 0.125 | 64 | 0.5 | 8 | 0.25 | 2 | 16 |
| *Strept. faec.* 27101 | 16 | 128 | 128 | >128 | 64 | 128 | >256 | 64 |
| *Strept. faec.* 113 | 16 | 32 | 64 | 128 | 120 | 64 | >256 | 128 |
| Enterococ. 9790 | 8 | 32 | 32 | 64 | 32 | 64 | >256 | 64 |
| Enterococ. 27158 | 2 | 16 | 32 | 32 | 8 | 64 | >256 | 32 |

-continued

| Organisms | Examples 2a | 8 | 12a | 15a | 20 | 22 | 23 | Cefaclor |
|---|---|---|---|---|---|---|---|---|
| Psdm. F 41 | >128 | >128 | >128 | >128 | >128 | >128 | >256 | >128 |
| Psdm. Walter | >128 | >128 | >128 | >128 | >128 | >128 | >256 | >128 |
| Psdm. 7035 | >128 | >128 | >128 | >128 | >128 | >128 | >256 | >128 |
| Psdm. 7451 | >128 | >128 | >128 | >128 | >128 | >128 | >256 | >128 |
| *Enterob. cl.* 5605 | >128 | >128 | >128 | >128 | >128 | >128 | >256 | >128 |
| *Enterob. cl.* 5744 | 128 | 32 | 8 | 64 | 64 | 16 | >256 | 8 |
| Achorob. 2005 | 0.25 | 0.5 | >0.06 | 2 | 0.25 | 0.5 | 0.5 | 0.25 |

It is possible, for example, to treat and/or prevent local and/or systemic diseases which are caused by the abovementioned pathogens or by mixtures thereof. The following may be mentioned as examples of diseases which can be prevented, improved and/or cured by the compounds according to the invention:

Diseases of the respiratory tract and of the pharyngeal cavity; otitis; pharyngitis; pneumonia, peritonitis; pyelonephritis; cystitis; endocarditis; systemic infections; bronchitis; arthritis; local infections.

The present invention includes pharmaceutical preparations which in addition to non-toxic, inert pharmaceutically suitable excipients contain one or more compounds according to the invention or which consist of one or more active compounds according to the invention, and processes for the production of these preparations.

The present invention also includes pharmaceutical preparations in dosage units. This means that the preparations are in the form of individual parts, for example tablets, coated tablets, capsules, pills, suppositories and ampules of which the content of active substance corresponds to a fraction or a multiple of an individual dose. The dosage units can contain, for example, 1, 2, 3 or 4 individual doses or ½, ⅓ or ¼ of an individual dose. An individual dose preferably contains the amount of active compound which is given in one administration and which usually corresponds to a whole, a half or a third or a quarter of a daily dose.

By non-toxic, inert pharmaceutically suitable excipients there are to be understood solid, semi-solid or liquid diluents, fillers and formulation auxiliaries of all kinds.

Tablets, coated tablets, capsules, pills, granules, suppositories, solutions, suspensions and emulsions, pastes, ointments, gels, creams, lotions, powders and sprays may be mentioned as preferred pharmaceutical preparations.

Tablets, coated tablets, capsules, pills and granules can contain the active compound or compounds alongside the customary excipients such as (a) fillers and extenders, for example starch, lactose, sucrose, glucose, mannitol and silica, (b) binders, for example carboxymethylcellulose, alginates, gelatine and polyvinylpyrrolidone, (c) humectants, for example glycerol, (d) disintegrating agents, for example agar-agar, calcium carbonate and sodium carbonate, (e) solution retarders, for example paraffin, and (f) absorption accelerators, for example quaternary ammonium compounds, (g) wetting agents, for example cetyl alcohol or glycerol monostearate, (h) adsorbents, for example kaolin and bentonite and (i) lubricants, for example talc, calcium and magnesium stearate and solid polyethylene glycols, or mixtures of the substances listed under (a) to (i).

The tablets, coated tablets, capsules, pills and granules can be provided with the customary coatings and shells, optionally containing opacifying agents, and can also be of such composition that they release the active compound or compounds only, or preferentially, in a certain part of the intestinal tract, optionally in a delayed manner, examples of embedding compositions which can be used being polymeric substances and waxes.

The active compound or compounds, optionally together with one or more of the abovementioned excipients, can also be in a microencapsulated form.

Suppositories can contain, in addition to the active compound or compounds, the customary water-soluble or water-insoluble excipients, for example polyethylene glycols, fats, for example cacao fat, and higher esters (for example $C_{14}$-alcohol with $C_{16}$-fatty acid) or mixtures of these substances.

Ointments, pastes, creams and gels can contain the customary excipients in addition to the active compound or compounds, for example animal and vegetable fats, waxes, paraffins, starch, tragacanth, cellulose derivatives, polyethylene glycols, silicones, bentonites, silica, talc and zinc oxide or mixtures of these substances.

Powders and sprays can contain the customary excipients in addition to the active compound or compounds, for example latose, talc, silica, aluminum hydroxide, calcium silicate and polyamide powders or mixtures of these substances. Sprays can additionally contain the customary propellants, for example chlorofluorohydrocarbons.

Solutions and emulsions can contain the customary excipients in addition to the active compound or compounds, such as solvents, solubilizing agents and emulsifiers, for example water, ethyl alcohol, isopropyl alcohol, ethyl carbonate, ethyl acetate, benzyl alcohol, benzyl benzoate, propylene glycol, 1,4-butylene glycol, dimethylformamide, oils, especially cottonseed oil, groundnut oil, corn germ oil, olive oil, castor oil and sesame oil, glycerol, glycerol-formal, tetrahydrofurfuryl alcohol, polyethylene glycols and fatty acid esters of sorbitan, or mixtures of these substances.

For parenteral administration, the solutions and emulsions can also be in a sterile form which is isotonic with blood.

Suspensions can contain the customary excipients in addition to the active compound or compounds, such as liquid diluents, for example water, ethyl alcohol or propylene glycol, suspending agents, for example ethoxylated isostearyl alcohols, polyoxyethylene sorbitol esters and sorbitan esters, microcrystalline cellulose, aluminum metahydroxide, bentonite, agar-agar and tragacanth, or mixtures of these substances.

The formulation forms mentioned can also contain dyestuffs, preservatives and additives which improve the odor and flavor for example peppermint oil and eucalyptus oil, and sweeteners, for example saccharin.

The therapeutically active compounds should preferably be present in the abovementioned pharmaceutical preparations in a concentration of about 0.1 to 99.5, preferably of about 0.5 to 95, percent by weight of the total mixture.

The abovementioned pharmaceutical preparations can also contain other pharmaceutical active compounds in addition to the compounds according to the invention.

The abovementioned pharmaceutical preparations are manufactured in the usual manner according to known methods, for example by mixing the active compound or compounds with the excipient or excipients.

The active compounds or the pharmaceutical preparations can be administered locally, orally, parenterally, intraperitoneally and/or rectally, preferably orally or parenterally, such as intravenously or intramuscularly.

In general it has proved advantageous both in human medicine and in veterinary medicine to administer the active compound or compounds in amounts of about 5 to 1,000, preferably 10 to 200, mg/kg of body weight every 24 hours, optionally in the form of several individual administrations, in order to achieve the desired results. An individual administration contains the active compound or compounds preferably in amounts of about 1 to about 250, in particular 3 to 60, mg/kg of body weight. However, it can be necessary to deviate from the dosages mentioned and, in particular, to do so as a function of the nature and body weight of the subject to be treated, the nature and the severity of the illness, the nature of the preparation and of the administration of the medicine, and the time or interval over which the administration takes place. Thus, it can suffice in some cases to manage with less than the abovementioned amount of active compound while in other cases the abovementioned amount of active compound must be exceeded. The particular required optimum dosage and the type of administration of the active compounds can easily be decided by anyone skilled in the art, on the basis of his expert knowledge.

In the case of use as feedstuff additives, it is possible for the new compounds to be administered in the customary concentrations and preparations together with the feedstuff or with feedstuff preparations or with the drinking water. It is possible by this means to prevent, improve and/or cure an infection by Gram-negative or Gram-positive bacteria, and likewise it is possible to achieve a promotion of growth and an improvement in the utilization of the feedstuff.

The new compounds are distinguished by potent anti-bacterial effects, which have been tested in vivo and in vitro, and by oral absorbability.

It is also possible for the purpose of extending the spectrum of action and increasing the action to combine the compounds according to the invention with other antimicrobial active compounds and lactamase inhibitors, for example with clavulanic acid and penicillins which are particularly penicillinase-resistant- or with aminoglyoside antibiotics such as aminoglycoside antibiotics such as, for example, gentamicin, sisomicin, kanamicin, amikacin or tobramicin.

The invention is demonstrated further by means of the examples which follow:

EXAMPLE 1

DL-7-(2-Aminobenzothiazol-6-ylglycylamido)-3-chloro-3-cephem-4-carboxylic acid

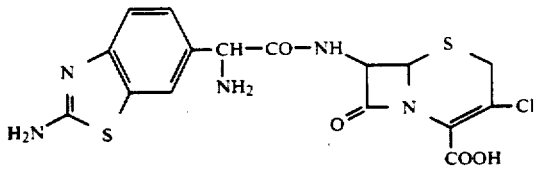

(a)

2-Amino-6-hydroxymethylbenzothiazole (1a)

50 g (0.225 mol) of ethyl 2-aminobenzothiazole-6-carboxylate are suspended in 1,000 ml of THF, cooled to −70° C., and 562.5 ml (0.675 mol) of diisobutylaluminum hydride (DIBAL, 20% strength in toluene, 1.2 molar) are slowly added dropwise under nitrogen. The reaction solution is stirred at −70° C. to −40° C. overnight and then without cooling for a further 3 hours. Then it is cooled to −70° C., 61.5 ml of water are added dropwise (vigorous exothermic reaction), and the mixture is allowed to reach room temperature. 305 ml of saturated sodium chloride solution are added, and the mixture is stirred at 20° C. for 1 hour. Precipitated aluminum hydroxide is filtered off with suction and washed with THF, and the filtrate is evaporated to dryness (36 g). The residue is dissolved in boiling ethanol, some insolubles are filtered off, and the filtrate is evaporated to dryness.

Yield: 25.5 g (63%).

$C_8H_8N_2OS$ (180.2)

NMR (DMSO): δ=4.5 (d, 2H), 5.13 (t, 1H), 7.18 (d, 1H), 7.3 (d, 1H), 7.4 (s, 2H), 7.59 (s, 1H) ppm.

(b)

2-Aminobenzothiazole-6-carboxaldehyde (1b)

110.5 g (0.613 mol) of 1a are stirred in 200 ml of THF with 319.8 g (3.678 mol) of manganese (IV) oxide at room temperature for 3 days. The reaction mixture is filtered, the residue on the filter is washed with THF, and the filtrate is evaporated in vacuo.

Yield: 74 g (68%).

$C_8H_6N_2OS$ (178.1).

NMR (DMSO): δ=7.48 (d, J=7.5 Hz, 1H), 7.8 (d, J=7.5 Hz, 1H), 8.08 (s, 2H), 8.26 (s, 1H), 9.92 (s, 1H) ppm.

(c)

5-(2-Aminobenzothiazol-6-yl)-2,4-imidazolidinedione (1c)

22.5 g (0.126 mol) of 1b, dissolved in 400 ml of methanol, are added dropwise to a solution of 50.9 g (0.531 mol) of ammonium carbonate and 9.6 g (0.196 mol) of sodium cyanide in 400 ml of water, and the mixture is stirred at 60° C. for 20 hours. After the methanol has been removed by distillation in vacuo, the remaining solution is acidified, at 0° C., to pH 2 with 2N HCl, then the pH is returned to 4 with 2N sodium hydroxide solution, and the precipitated product is filtered off with suction.

Yield: 20.5 g (65%).

$C_{10}H_8N_4O_2S$ (248.3).

calculated: C 48.38, H 3.25, N 22.56, S 12.91. found: C 48.4, H 3.5, N 21.2, S 12.3.

NMR (DMSO): $\delta=5.17$ (s, 1H), 7.17 (q, 1H), 7.35 (d, 1H), 7.57 (s, 1H), 7.62 (s, 1H), 8.4 (s, 1H), 10.6–10.82 (broad s, 1H) ppm.

(d)

DL-α-Amino-α-(2-aminobenzothiazol-6-yl)acetic acid (DL-6-aminobenzothiazolylglycine, (1d)

20 g (0.081 mol) of 1c are heated with 19.4 g (0.81 mol) of lithium hydroxide in 400 ml of water, with stirring, at 100° C. for 24 hours. The solution is filtered hot, the residue on the filter is washed with hot water, and the filtrate is acidified, while cooling in ice, to pH 2 with concentrated HCl. The mixture is stirred at 0° C. for 15 minutes, and the pH of the solution with the precipitated product is returned to 4.5. The precipitate is filtered off with suction, washed with water/acetone and dried in vacuo.

Yield: 10.4 g (56%)

$C_9H_9N_3O_2S.\frac{1}{2}H_2O$ (232.3): calculated: C 45.05, H 4.20, N 17.51, S 13.36. found: C 45.3, H 4.6, N 15.5, S 13.4.

NMR (DCOOD): $\delta=5.11$ (s, 1H), 7.8 (s, 2H) 8.11 (s, 1H) ppm.

(e)

DL-α-t-Butyloxycarbonylamino-α-(2-t-butyloxycarbonylaminobenzothiazol-6-yl)acetic acid (di-Boc derivative) and DL-α-t-Butyloxycarbonylamino-α-(2-aminobenzothiazol-6-yl)acetic acid (mono-Boc derivative) (1e)

20 g (0.0896 mol) of 1d are suspended in 100 ml of water and 130 ml of dioxane and induced to dissolve with 140 ml of 2N sodium hydroxide solution. Then 78.1 g (0.358 mol) of di-t-butyl dicarbonate are added dropwise within 30 minutes and stirred overnight. Dioxane is removed by distillation, and the remaining solution is diluted with $H_2O$ and washed with ethyl acetate/petroleum ether. The aqueous phase is acidified, while cooling in ice, to pH 2 with 2N HCl and is extracted twice with ethyl acetate/THF (1:1). After washing with sodium chloride solution, drying over $Na_2SO_4$ and evaporation of the organic phase, a mixture of the mono- and di-Boc derivatives is obtained.

Yield: 24.7 g.

Chromatography is carried out on silica gel (Merck, 0.04–0.063 mm) with eluting agents in the following sequence:

1. 2,000 ml $CH_2Cl_2$
2. 4,000 ml $CH_2Cl_2$/methanol (10:0.5)
3. $CH_2Cl_2$/methanol (10:1)
4. $CH_2Cl_2$/methanol (1:1)

Di-Boc derivative (1e):

Yield: 8.7 g (26%).

$C_{19}H_{25}N_3O_6S$ (423.5).

NMR (DMSO): $\delta=1.37$ (s, 9H), 1.52 (s, 9H), 5.12 (d, 1H), 7.45 (d, 2H), 7.65 (d, J=7.5 Hz, 1H), 7.96 (s, 1H) ppm.

Mono-Boc derivative:

Yield: 9.2 g (32%).

$C_{14}H_{17}N_3O_4S$ (323.4).

NMR (DMSO): $\delta=1.36$ (s, 9H), 4.98 (d, 1H), 7.2–7.3 (q, 2H), 7.48 (s, 2H), 7.54 (s, 1H) ppm.

(f)

DL-7-[2-(t-Butyloxycarbonylamino)-2-(2-t-butyloxycarbonylaminobenzothiazol-6-yl)acetamido]-3-chloro-3-cephem-4-carboxylic acid (1f)

Activation of the precursor acid:

5.1 g (12 mmol) of 1e are dissolved in 40 ml of DMF, 1.69 ml (12 mmol) of triethylamine are added, and, at −40° C., 1.48 ml (12 mmol) of pivaloyl chloride are injected dropwise, and the mixture is stirred at −30° C. to −15° C. for 3 hours.

Preparation of the amine component:

2.83 g (12 mmol) of 7-amino-3-chloro-3-cephem-4-carboxylic acid (7-ACCA) are suspended in 20 ml of THF and 10 ml of water and induced to dissolve with concentrated triethylamine (pH 8.3). Then 5 ml of DMF are added in order to obtain one phase.

Coupling and isolation:

The 7-ACCA solution is injected into the anhydride, which has been formed, at −40° C. and is stirred in a cooling bath. After 1 hour, 10–20 ml of $H_2O$ are added and the pH is adjusted to 7.3 with 10% triethylamine/THF. After a further 2 hours, 200 ml of $H_2O$ are added and, while stirring, ethyl acetate/THF (2:1) are added and the mixture is acidified to pH 1.7 at 0° C. The organic layer is separated off, washed with sodium chloride solution, dried and evaporated to 30 ml which is stirred into petroleum ether, and precipitated product is filtered off with suction and dried.

Yield: 6.2 g (81%), purity: 66% by HPLC.

$C_{26}H_{30}ClN_5O_8S_2$ (640.1).

NMR (DMSO): $\delta=1.39$ (s, 9H), 1.52 (s, 9H), 3.5–4.02 (broad m, 2H), 5.1–5.24 (dd, 1H), 5.38 (d, 1H), 5.62–5.8 (dd, 1H), 7.42–7.53 (m, 1H), 7.68 (d, 1H), 7.98 (s, 1H) ppm.

(g)

DL-7-(2-Aminobenzothiazol-6-ylglycylamido)-3-chloro-3-cephem-4-carboxylic acid (1 g)

8.4 g (13.1 mmol) of 1f are dissolved in 50 ml of methylene chloride and, at 0° C., 0.5 ml of anisole and 50 ml of trifluoroacetic acid (TFA) are added, and the mixture is stirred without cooling for 15 minutes. Then the trifluoroacetic acid/methylene chloride mixture is removed by distillation in vacuo, and ether is added to the oily residue. The trifluoroacetate is filtered off with suction, washed with ether and dried.

Yield: 6.5 g (89%).

$C_{16}H_{14}ClN_5O_4S_2.CF_3COOH$ (553.9).

HPLC purity: (Hibar 250-4, RP 8, 10 μm, 254 nm, 3 ml/min, eluting agent: 1,000 ml $H_2O$-40 ml acetonitrile-1 ml TFA).

Retention: 1.10 (1d, 10.8%), 3.08 (L-form, 46.5%), 3.82 (D-form, 38.5%).

EXAMPLE 2

D-7-(2-Aminobenzothiazol-6-ylglycylamido)-3-chloro-3-cephem-4-carboxylic acid and L-form (A)

Chromatographic separation 2.3 g of 1 g are dissolved in 50 ml of eluting agent (1,000 ml $H_2O$-50 ml acetonitrile-1 ml TFA) and 4 drops of TFA, the mixture is stirred for 20 minutes, insoluble material is filtered off with suction, and the filtrate is filtered once more using a syringe (Millex-GS, 0.22 μm, millipore) and pumped in 10 ml portions (460 mg) slowly onto a preparative column (Hibar 250-25, RP 18, 7 μm, flow rate 15 ml/min) in 10–15 minutes.

D-form (peak II):

Yield 350 mg of trifluoroacetate.

A total of 4.3 g of trifluoroacetate are dissolved in 500 ml of water and applied to a column containing 25 ml of Amberlite IRA-68 (acetate form), and elution is carried out with 1.5 l of water (distilled). The eluate is evaporated to 1,000 ml and filtered with suction through a 0.45 μm millipore filter and the product is freeze-dried.

Yield: 3.0 g (75%)

$C_{16}H_{14}ClN_5O_4S_2.3H_2O.0.5CH_3COOH$ (523.9): calculated: C 38.97, H 4.23, N 13.36, S 12.24, Cl 6.76. found: C 38.9, H 4.0, N 13.6, S 12.0, Cl 6.8.

HPLC purity: 97.4% Hibar 250-4, RP 8, 10 μm, 254 nm, 3 ml/min, 0.5 mg/ml, eluting agent: 1,000 ml $H_2O$-30 ml $CH_3COOH$).

NMR (DCOOD): δ=3.58 (d, J=18 Hz, 1H), 3.94 (d, J=18 Hz, 1H), 5.32 (d, J=5 Hz, 1H), 5.75 (s, 1H), 5.94 (d, J=5 Hz, 1H), 7.84 (s, 2H), 8.12 (s, 1H) ppm.

L-form (peak I)

Yield 400 mg of trifluoroacetate.

A total of 2.01 g of trifluoroacetate are dissolved in 500 ml of water, applied onto a column containing 30 ml of Amberlite IRA-68 (acetate form), and elution is carried out with 1.5 l of $H_2O$ (distilled). The eluate is evaporated to 1,000 ml, and the product is freeze-dried.

Yield: 1.08 g (60%).

$C_{16}H_{14}ClN_5O_4S_2.3H_2O$ (493.9): calculated: C 38.90, H 4.08, N 14.17. found: C 38.6, H 3.7, N 13.3.

HPLC purity: 94.5% (Hibar 250-4, RP 8, 10 μm, 254 nm, 1.8 ml/min, eluting agent: 930 ml $H_2O$-20 ml buffer pH 7 50 ml acetonitrile).

NMR (DCOOD): δ=3.78 (d, J=17.5 Hz, 1H), 4.03 (d, J=17.5 Hz, 1H), 5.4 (d, J=5 Hz, 1H), 5.8 (s, 1H), 5.92 (d, J=5 Hz, 1H), 7.87 (s, 2H), 8.2 (s, 1H) ppm.

(B)

D-Phenylglycine as starting material for D-7-(2-aminobenzothiazol-6-ylglycylamido)-3-chloro-3-cephem-4-carboxylic acid (a)

D-α-Acetamido-α-phenylacetic acid (2a)

500 g (3.31 mol) of D-α-amino-α-phenylacetic acid are suspended in 6 liters of water, and the suspension is cooled to 10° C. and 132 g (3.31 mol) of NaOH dissolved in 1,000 ml of water are added. After 15 minutes, 675 g (6.62 mol) of acetic anhydride and then 397 g (9.93 mol) of NaOH—dissolved in 1,000 ml of water—are poured into the clear solution at 0° C., stirring rapidly. The temperature increases from 0° C. to 30° C. during this. The solution is stirred for a further 20 minutes at pH 9 to 10 in an ice/sodium chloride bath and is then acidified to pH 1 with concentrated hydrochloric acid (about 1 liter). The suspension is then stirred for 10 minutes, cooled to 10° C., filtered with suction and washed with 10 liters of water. The product is dried over KOH in vacuo.

Yield: 553 g (87%).

$C_{10}H_{11}NO_3$ (193.2).

Melting point 190°–191° C.

$[\alpha]_{589}^{20°}=-218.6°$ (C=1, $C_2H_5OH$).

(b)

D-α-Acetamido-α-(4-nitrophenyl)acetic acid and D-α-acetamido-α-(3-nitrophenyl)acetic acid as a mixture of isomers (2b)

227 g (1.17 mol) of 2a are slowly added to 570 ml of concentrated sulphuric acid at 40° C. to 50° C. After the addition the mixture is stirred for a further 5 minutes at 40° C. and is then cooled to 0° C. 111.5 ml (2.39 mol of 95% strength nitric acid (d=1.5) are slowly added dropwise, at −5° C. to 0° C., within 30 to 45 minutes. The mixture is then stirred at −5° C. to −10° C. for 30 minutes, and the reaction solution tipped onto 8 liters of ice, and the precipitated product is filtered off with suction and washed with a large quantity of water.

Yield: 276.1 g (98%).

$C_{10}H_{10}N_2O_5$ (239.2).

$[\alpha]_{589}^{20}=-193.9°$ (C=1, $C_2H_5OH$).

(c)

D-α-Acetamido-α-(4-aminophenyl)acetic acid (2c)

240 g (1.0 mol) of the mixture of isomers 2b are dissolved in 3 liters of 95% ethanol and hydrogenation is carried out in the presence of 10 g of palladium on active charcoal (10%) at 23° C. and 10 atmospheres for 2 hours. 2.4 liters of water are added to the resulting suspension, which is heated to reflux and then filtered through kieselguhr with suction. The yellow microcrystalline mass which precipitates from the filtrate overnight is filtered off with suction, washed with a little ethanol/water (3:1) and dried.

Yield: 67.2 g.

$C_{10}H_{12}N_2O_3$ (208.2).

Melting point 208° C.–211° C.

$[\alpha]_{589}^{20°}=-186.1°$ (C=1, 1N HCl).

NMR (DMSO): δ=1.8 (s, 3H); 5.05 (d, 1H), 6.52 (d, J=8.5 Hz, 2H), 7.02 (d, J=8.5 Hz, 2H); 8.35 (d, 1H) ppm.

(d)

Methyl D-α-acetamido-α-(4-aminophenyl)acetate (2d)

67.7 g (0.33 mol) of 2c are suspended in 400 ml of methanol and, while stirring at −10° C. to −5° C., 34.9 ml (0.487 mol) of thionyl chloride are added dropwise, whereupon a clear orange solution is produced. The temperature of the solution is allowed to rise to 25° C. overnight and it is then evaporated to dryness in vacuo. The residue is partitioned between 1,000 ml of ethyl acetate and 800 ml of 10% strength $NaHCO_3$ solution, and the pH is adjusted to 7.5 with 2N sodium hydroxide solution. The ethyl acetate phase is separted off, and the aqueous phase is extracted twice more with ethyl acetate, and the combined extracts are washed with sodium chloride solution. 48.1 g (67%) are obtained after drying and removal of the solvent by evaporation.

$C_{11}H_{14}N_2O_3$ (222.2).

$[\alpha]_{589}^{20°}=-222.2°$ (C=1, $C_2H_5OH$).

NMR (DMSO): δ=1.85 (s, 3H); 3.55 (s, 3H), 5.1 (d, 1H), 5.15 (s, 2H); 6.52 (d, J=9 Hz, 2H), 6.97 (d, J=9 Hz, 2H); 8.45 (d, 1H) ppm.

(e)

Methyl D-α-acetamido-α-(2-aminobenzothiazol-6-yl)acetate (2e)

47.8 g (0.206 mol) of 2d are suspended in 620 ml of glacial acetic acid, and 80 g (0.823 mol) of solid KSCN are added. After stirring at room temperature for 45 minutes a clear solution forms, and this is cooled to 10° C. and 11.6 ml (0.226 mol) of bromine—dissolved in 100 ml of glacial acetic acid—are added dropwise in 15 minutes. The mixture is then stirred at 10° C. to 15° C. for 1 hour. Glacial acetic acid is removed by distillation in vacuo from the mass of crystals which has formed, and the residue is suspended in 1,000 ml of water and the pH is adjusted to 6.3 with $Na_2CO_3$. The mixture is then stirred at 70° C. to 80° C. for 2 hours, extracted several times with ethyl acetate, and the combined ethyl acetate phases are washed with sodium chloride solution and dried over $Na_2SO_4$.

Yield: 33.8 g (59%).

$C_{12}H_{13}N_3O_3S$ (279.3): calculated: C 51.5, H 4.7, N 15.0, S 11.5. found: C 52.0, H 5.5, N 14.2, S 11.0.

$[\alpha]_{589}^{20°} = -126.0°$ (C=1, $C_2H_5OH$).

NMR (DMSO): δ=2.19 (s, 3H), 3.62 (s, 3H), 5.35 (d, 1H), 7.2 (d, 1H) 7.33 (d, 1H) 7.54 (s, 2H), 7.65 (d, 1H), 8.67 (d, 1H) ppm.

(f)

D-α-Amino-α-(2-aminobenzothiazol-6-yl)acetic acid dihydrochloride (2f)

70 g (0.251 mol) of 2e are stirred in 700 ml of 6N hydrochloric acid at 40° C. for 40 minutes. The clear solution which has thus been produced is stirred at 110° C. for a further 1½ hours, then cooled to 0° C. and evaporated to 200 ml. 1,000 ml of acetone are added to the mass of crystals which have formed, and the precipitate is filtered off with suction, washed with acetone and dried over $P_4O_{10}$.

Yield: 34.9 g (47%).

$C_9H_9N_3O_2S$ 2 HCl (296.2). calculated: C 36.4, H 3.75, N 14.1, S 10.8, Cl 23.9. found: C 35.5, H 4.1, N 13.5, S 10.9, Cl 23.5.

$[\alpha]_{589}^{20°} = -84.4°$ (C=1, 1N, HCl).

NMR ($D_2O$): =5.25 (s, 1H); 7.58 (t, 2H), 7.88 (s, 1H) ppm.

Further product of the same purity can be obtained by evaporation of the mother liquor and digestion of the resulting mass of crystals with acetone.

Yield: 20 g (27%).

$[\alpha]_{589}^{20°} = -78.7°$ (C=1, 1N HCl).

(g)

D-α-t-Butoxycarbonylamino-α-(2-aminobenzothiazol-6-yl)acetic acid (2 g)

36.3 g (0.166 mol, 2.45 equivalents) of di-t-butyl dicarbonate are added to 20 g (0.0675 mol) of 2f in 310 ml of 10% strength lithium hydroxide solution and 210 ml of dioxane, and the mixture is then stirred at pH 10 overnight. The precipitated lithium carbonate is filtered off with suction and washed with warm water (300 ml). The filtrate is evaporated to 150 ml, acidified to pH 3.5 with 2N HCl and extracted twice with ethyl acetate/THF (10:1). The combined extracts are washed with sodium chloride solution, dried over $MgSO_4$, and the solution is evaporated to 100 ml and 500 ml of n-hexane are added. The precipitated product is filtered off with suction, washed with n-hexane and dried over KOH in vacuo.

Yield: 15.9 g.

$C_{14}H_{17}N_3O_4S.H_2O$ (341.3): calculated: C 49.3, H 5.6, N 12.3, S 9.4. found: C 48.2, H 5.3, N 11.3, S 10.0.

$[\alpha]_{589}^{20°} = -130.9°$ (C=1, $CH_3OH$).

NMR (DMSO): δ=1.4 (s, 9H); 5.1 (d, 1H); 7.25–7.34 (dd, 2H) 7.53 (d, 1H), 7.71 (s, 1H), 7.98 (s, 2H) ppm.

(h)

D-7-(2-Aminobenzothiazol-6-ylglycylamido)-3-chloro-3-cephem-4-carboxylic acid (2h)

15.5 g (0.0479 mol) of 2 g in 220 ml of DMF are reacted with 6.78 ml (0.0479 mol) of triethylamine and 5.89 ml (0.0479 mol) of pivaloyl chloride in analogy to Example 1f. The mixed anhydride is added dropwise, within 15 minutes, to a solution of the triethylammonium salt of 7-ACCA, which is prepared by vigorously stirring 11.24 g (0.0479 mol) of 7-ACCA in 110 ml of THF and 110 ml of $H_2O$ by dropwise addition of triethylamine, at −10° C. During the addition of the mixed anhydride, the pH is kept constant at 7.5 by triethylamine dissolved in water/THF (1:1) at the same time. The isolation of the Boc-protected cephalosporin and the deblocking are carried out in analogy to Example 1f.

Yield: 13.4 g (51%, crude product).

$C_{16}H_{14}ClN_5O_4S_2.CF_3COOH$ (553.9).

After preparative HPLC separation of the crude product on a Whatman column (Magnum M40, 500×40, Partisil ODS-3, 50 μm) with 2% strength acetic acid as the eluting agent, 4.3 g are obtained.

$C_{16}H_{14}ClN_5O_4S_2.2H_2O.\frac{1}{3}CH_3COOH$ (495.9): calculated: C 40.36, H 3.93, N 14.12, S 12.9. found: C 40.5, H 3.9, N 12.9, S 12.0.

NMR (DCOOD): δ=3.58 (d, J=18 Hz, 1H); 3.94 (d, J=18 Hz, 1H); 5.32 (d, J=5 Hz, 1H); 5.75 (s, 1H), 5.94 (d, J=5 Hz, 1H), 7.84 (s, 2H), 8.12 (s, 1H) ppm.

EXAMPLE 3

DL-7-(2-Aminobenzothiazol-6-ylglycylamido)-3-methyl-3-cephem-4-carboxylic acid

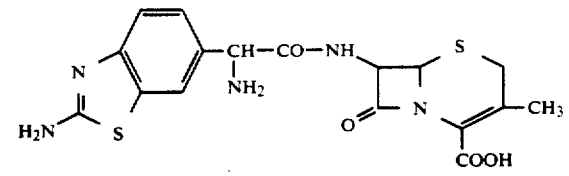

2.16 ml (12.4 mmol) of ethyldiisopropylamine and 0.96 ml (12.4 mmol) of methanesulphonyl chloride are successively injected slowly into a solution, cooled to −50° C., of 4.0 g (12.4 mmol) of 1e (mono-Boc derivative) in 30 ml of DMF/30 ml of THF. The mixture is stirred at −50° C. for 45 minutes and a solution (0° C.) of 3.35 g (12.4 mmol) of t-butyl 7-amino-3-methyl-3-cephem-4-carboxylate and 2.16 ml (12.4 mmol) of ethyldiisopropylamine in 25 ml of THF and 25 ml of methylene chloride are added dropwise. The mixture is then stirred at −50° C. for 15 minutes and then without cooling for a further 45–60 minutes. The solvent is then removed by distillation in vacuo, and the residue is dissolved in 300 ml of ethyl acetate and the solution is washed with 0.1N hydrochloric acid, sodium chloride solution, $NaHCO_3$ solution and water. 3.2 g (45%) are obtained after drying and removal of the solvent by distillation.

1.5 g (2.6 mmol) of Boc-protected cephalosporin are dissolved in 30 ml of $CH_2Cl_2$ and, at 0° C., 0.5 ml of anisole and 30 ml of TFA are added, and the mixture is stirred at room temperature for 1 hour. Then the TFA/$CH_2Cl_2$ mixture is removed by distillation in vacuo, and ether is added to the oily residue. The trifluoroacetate is filtered off with suction, washed with ether, dried and then taken up in 200 ml of water and applied to a column of Amberlite IRA-68 (acetate form). The column is washed with 200 ml of water and the eluate is freeze-dried.

Yield: 764 mg.

$C_{17}H_{17}N_5O_4S_2$ (419.5).

NMR (DCOOD: δ=2.16 (d, 3H), 3.2–3.64 (mm, 2H), 5.18–5.26 (dd, 1H), 5.72–5.85 (m and d, 2H), 7.32 (m, 2H), 8.16 (d, 1H) ppm.

EXAMPLE 4

D-7-(2-Aminobenzothiazol-6-ylglycylamido)-3-methyl-3-cephem-4-carboxylic acid (4a) and L-form (4b)

400 mg of 3 are separated into the D- and L-forms on a preparative Zorbax column (Dupont 250-21, ODS, 8 μm, 230 nm, eluting agent 93% 0.1% TFA in $H_2O$-7% methanol).

L-form (peak I):

After elution, the L-form is first obtained as peak I.

Yield: 110 mg.

The trifluoroacetate is dissolved in 50 ml of $H_2O$, applied to a column of Amberlite IRA-68 (acetate form), and is eluted with 200 ml of $H_2O$ and freeze-dried.

Yield: 55 mg.

$C_{17}H_{17}N_5O_4S_2$ (419.5).

NMR (DCOOD): δ=2.26 (s, 3H), 3.48 (d, J=18 Hz, 1H), 3.62 (d, J=18 Hz, 1H), 5.26 (d, J=5 Hz, 1H), 5.78 (s, 1H), 5.82 (d, J=5 Hz, 1H), 7.84 (q, 2H), 8.18 (s, 1H) ppm.

D-form (peak II):

The D-form is obtained as peak II by further elution with 0.1% trifluoroacetic acid/methanol.

Yield: 71 mg.

The trifluoroacetate is converted into the betaine using Amberlite IRA-68 (acetate form).

Yield: 47.3 mg

NMR (DCOOD): δ=2.19 (s, 3H), 3.3 (d, J=18 Hz, 1H), 3.5 (d, J=18 Hz, 1H), 5.2 (d, J=5 Hz, 1H), 5.75 (s, 1H), 5.86 (d, J=5 Hz, 1H) 7.84 (s, 2H), 8.16 (s, 1H) ppm.

EXAMPLE 5

DL-7-(2-Amino-6-methylbenzothiazol-4-ylglycylamido)-3-chloro-3-cephem-4-carboxylic acid

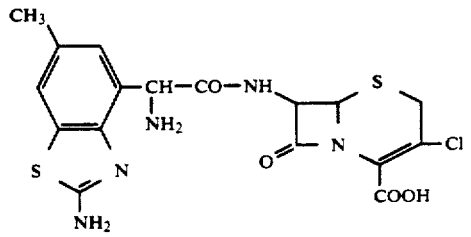

(a)

Methyl 2-amino-6-methylbenzothiazole-4-carboxylate (5a)

50 g (0.303 mol) of methyl 2-amino-5-methylbenzoate are dissolved in 300 ml of glacial acetic acid, and 120.6 g (1.24 mol) of potassium thiocyanate—dissolved in 200 ml of glacial acetic acid—are added. At 10° C., 17.42 ml (0.335 mol) of bromine are added dropwise, and the mixture is then stirred without cooling for 2 hours. The suspension is tipped into 3 l of ice-water, while stirring, and the precipitated product is filtered off with suction and washed with dilute sodium carbonate solution and water. The filter cake is suspended in $H_2O$ and the suspension is stirred at 100° C. overnight. After cooling, the product is filtered off with suction, washed with $H_2O$ and dried at 40° C. in vacuo.

Yield: 60 g (89%).

$C_{10}H_{10}N_2O_2S$ (222.2).

NMR (DMSO): =2.35 (s, 3H), 3.8 (s, 3H), 7.5 (s, 1H), 7.71 (s, 1H), 7.81 (s, 2H) ppm.

(b)

2-Amino-4-hydroxymethyl-6-methylbenzothiazole (5b)

30 g (0.135 mol) of 5a are reduced with 337.7 ml (0.405 mol) of DIBAL (20% strength solution in toluene) in analogy to Example 1a.

Yield: 21.2 g (81%).

$C_9H_{10}N_2OS$ (194.2).

NMR (DMSO): =2.35 (s, 3H), 4.72 (d, 1H), 5.05 (t, 2H), 7.12 (s, 1H), 7.34 (s, 1H), 7.41 (s, 2H) ppm.

(c)

2-Amino-6-methylbenzothiazole-4-carboxaldehyde (5c)

67.6 g (0.348 mol) of 5b are treated with 241 g (2.77 mol) of manganese(IV) oxide in analogy to Example 1b.

Yield: 33.6 g (50%).

$C_9H_8N_2OS$ (192.2).

NMR (DMSO): δ=2.39 (s, 3H), 7.45 (s, 1H), 7.79 (s, 1H), 8.01 (s, 2H), 10.6 (s, 1H) ppm.

(d)

5-(2-Amino-6-methylbenzothiazol-4-yl)-2,4-imidazolidinedione (5d)

36.2 g (0.188 mol) of 5c are reacted with 75.9 g (0.791 mol) of ammonium carbonate and 14.3 g (0.292 mol) of sodium cyanide in analogy to Example 1c.

Yield: 25.5 g (52%)

$C_{11}H_{10}N_4O_2S$ (262.3): calculated: C 50.37, H 3.84, N 21.36, S 12.22. found: C 51.2, H 5.0, N 21.0, S 11.2.

NMR (DCOOD): δ=2.28 (s, 3H), 5.87 (s, 1H), 7.43 (s, 1H), 7.48 (s, 1H), 7.64 (s, 2H) ppm.

(e)

DL-α-Amino-α-(2-amino-6-methylbenzothiazol-4-yl)acetic acid (5e)

25.5 g (97.2 mmol) of 5d in 500 ml of hydrobromic acid (48%) are heated under reflux for 24 hours. The reaction solution is then evaporated to dryness, the residue is taken up in $H_2O$, and the aqueous phase is washed twice with ethyl acetate and evaporated to dryness in vacuo.

Yield: 38.1 g $C_{10}H_{11}N_3O_2S.2HBr.2H_2O$ (435.1): calculated: C 27.60, H 3.94, N 9.65, S 7.36, Br 36.73. found: C 26.9, H 3.9, N 10.2, S 6.5, Br 40.8.

(f)

DL-α-t-Butyloxycarbonylamino-α-(2-amino-6-methylbenzothiazol-4-yl)acetic acid (5f)

34.7 g (0.09 mol) of 5e are stirred with 98.2 g (0.45 mol) of di-t-butyl dicarbonate at room temperature for 4 days in analogy to Example 1e.

Crude yield: 19.8 g (50%), 6 g after recrystallization from methanol.

$C_{15}H_{19}N_3O_4S$ (337.4).

NMR (DMSO): δ=1.37 (s, 3H), 5.57 (d, 1H), 7.0 (s, 1H), 7.25 (d, 1H), 7.35 (s, 1H), 7.52 (s, 2H) ppm.

(g)

DL-7-(2-Amino-6-methylbenzothiazol-4-ylglycylamido)-3-chloro-3-cephem-4-carboxylic acid (5g)

3.37 g (0.01 mol) of 5f are reacted with 1.4 ml (0.01 mol) of triethylamine, 1.23 ml (0.01 mol) of pivaloyl chloride and 2.34 g (0.01 mol) of 7-ACCA in analogy to Example 1f.

The Boc-protected cephalosporin is deblocked in analogy to Example 1g. The substance is treated with Amberlite IRA-68 (acetate form) to remove TFA and is freeze-dried.

Yield: 830 mg (16%).

$C_{17}H_{16}ClN_3O_4S_2.3H_2O$ (507.9).

NMR (DCOOD): δ=2.49 (d, 3H), 3.58–4.02 (mm, 2H), 5.36 (dd, 1H), 5.83–5.94 (m, 2H), 7.56 (m, 1H), 7.84 (m, 1H) ppm.

EXAMPLE 6

DL-6-(2-Aminobenzothiazol-6-ylglycylamido)-penicillanic acid

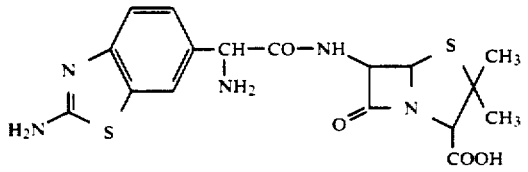

(a)

DL-α-Benzyloxycarbonylamino-α-(2-aminobenzothiazol-6-yl)acetic acid (6a)

5 g (16.9 mmol) of dihydrochloride 1d are suspended in 100 ml of water and heated at 100° C. with 4.25 g (50.7 mmol) of sodium bicarbonate. Then, 2N sodium hydroxide solution is added until the pH is 9. 4.8 g (17.7 mmol) of benzyl p-nitrophenyl carbonate—dissolved in 100 ml of dioxane—are added, and the mixture is stirred at 100° C. for 3 hours. The solution is filtered hot, and dioxane is removed from the filtrate in vacuo and the latter is washed twice with ethyl acetate. The aqueous phase is acidified to pH 3.8 at 10° C. with 2N HCl, and the precipitated product is filtered off with suction, dried at 40° C. and then digested in boiling acetone and, at 20° C., ether is added and the product is filtered off with suction.

Yield: 3 g (50%).

$C_{17}H_{15}N_3O_4S$ (357.4).

NMR (DMSO): δ=5.07 (s, 2H), 5.18 (d, J=7.5 Hz, 1H) 7.36 (m, 7H), 7.73 (s, 1H), 7.96 (s, 2H), 8.08 (d, 1H) ppm.

(b)

Allyl DL-6-[α-benzyloxycarbonylamino-α-(2-aminobenzothiazol-6-ylglycylamido)]penicillanate (6b)

0.98 ml (5.6 mmol) of ethyldiisopropylamine and 0.44 ml (5.6 mmol) of methanesulphonyl chloride are successively slowly injected into a solution, cooled to −50° C., of 2.0 g (5.6 mmol) of 6a in 32 ml of THF. The mixture is stirred at −50° C. for 45 minutes and then a solution of 2.52 g (5.88 mmol) of the p-toluenesulphonic acid salt of allyl 6-aminopenicillanate and 1.02 ml (5.88 mmol) of ethyldiisopropylamine in 32 ml of THF is added dropwise. The mixture is stirred at −50° C. for 15 minutes and then for a further 45–60 minutes without cooling. The solvent is then removed by distillation in vacuo, the residue is taken up in 300 ml of ethyl acetate, and the solution is washed with 0.1N HCl, sodium chloride solution, $NaHCO_3$ solution and water. After drying and removal of the solvent by evaporation, 2.2 g (66%) of 4b are obtained.

$C_{28}H_{29}N_5O_6S_2$ (595.7)

NMR (DMSO): δ=1.32–1.60 (mm, 6H), 4.4 (d, 1H), 4.67 (d, 2H), 5.05 (d, 2H), 5.3 (dd, 1H), 5.39–5.57 (mm, 4H), 5.95 (mm, 1H), 7.3 (m, 7H), 7.5 (d, 2H), 7.7 (d, 1H), 7.98 (m, 1H), 9.03 (q, 1H) ppm.

(c)

DL-6-[α-Benzyloxycarbonylamino-α-(2-aminobenzothiazol-6-ylglycylamido)]penicillanic acid (6c)

Successively 10.6 ml (5.3 mmol) of 0.5M sodium caprylate solution in ethyl acetate are injected, and 92.6 mg (0.353 mmol, 0.1 equivalent) of triphenylphosphine are added, to a solution of 2.1 g (3.53 mmol) of 6b in 12 ml of $CH_2Cl_2$ under nitrogen. After 2 minutes, 93.6 mg (0.081 mmol, 2.3 mol % of 6b) of tetrakis(triphenylphosphine)palladium (O) are added, and the mixture is stirred at room temperature for 20 minutes, whereupon the sodium salt crystallizes out. Acetone is added, and the product is filtered off with suction and washed with acetone and ether.

Yield: 1.8 g (87%).

$C_{25}H_{24}NaN_5O_6S_2$ (577.6).

NMR (DMSO): δ=1.42–1.6 (q, 6H), 3.88 (d, 1H), 5.08 (s, 2H), 5.32 (d, 1H), 5.42 (d, 1H), 5.54 (d, 1H), 7.4 (m, 7H), 7.57 (s, 2H) 7.75 (s, 1H) ppm.

(d)

Sodium DL-6-(2-aminobenzothiazol-6-ylglycylamido)penicillanate (6d)

5.4 g (9.35 mmol) of 6c are dissolved in 200 ml of $H_2O$ with the addition of 15 ml of n-butanol, and deacylation is carried out by hydrogenolysis in a prehydrogenated aqueous solution over 30 g of palladium black in 60 minutes. After removal of the catalyst and removal of n-butanol by distillation, the aqueous filtrate is freeze-dried.

Yield: 3.4 g (83%).

$C_{17}H_{18}NaN_5O_4S_2$ (443.5).

NMR (DMSO): δ=1.47–1.62 (q, 6H), 3.97 (d, 1H), 5.0 (broad d, 1H), 5.4 (d, 1H), 5.48 (d, 1H), 7.28 (s, 2H), 7.51 (s, 2H), 7.68 (s, 1H) ppm.

EXAMPLE 7

D-6-(2-Aminobenzothiazol-6-ylglycylamido)penicillanic acid 3.4 g of 6d are separated into the D- and L-forms on a preparative Zorbax column (Dupont 250-21, ODS, 8 μm, 240 nm). The mobile phase used is 9 g of $NaH_2PO_4$ in 1,000 ml of water/methanol (86:14). Methanol is removed from the eluate (peak II) by distillation and, to remove salt, the remaining solution is applied to a Lobar column (size B, RP-8) and elution is first carried out with water. The column is then rotated by 180° C., washed with acetonitrile, and the eluate is evaporated to dryness in vacuo.

Yield: 120 mg.

NMR (DMSO): δ=1.38 (s, 3H), 1.48 (s, 3H), 4.22 (s, 1H), 5.01 (s, 1H), 5.31 (d, J=5 Hz, 1H), 5.4 (d, J=5 Hz, 1H), 7.3 (m, 2H), 7.64 (s, 2H), 7.72 (s 1H) ppm.

EXAMPLE 8

DL-7-(Benzimidazol-5(6)-ylglycylamido)-3-chloro-3-cephem-4-carboxylic acid

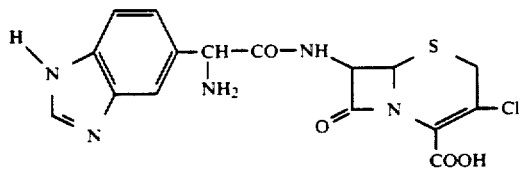

(a)

5(6)-Hydroxymethylbenzimidazole (8a)

1150.3 ml (1.38 mol) of DIBAL (20% strength solution in toluene, Schering) are added, at 0° C., to 40 g (0.227 mol) of methyl benzimidazole-5(6)-carboxylate in THF in analogy to Example 1a, and stirred overnight at room temperature.

Yield: 22.5 g (67%).

$C_8H_8N_2O$ (148.2).

NMR (DMSO): δ=4.61 (s, 2H), 5.22 (broad s, 1H), 7.18 (d, 1H), 7.56 (d, 2H), 8.2 (s, 1H), 12.42 (s, 1H) ppm.

(b)

Benzimidazole-5(6)-carboxaldehyde (8b)

42.3 g (0.285 mol) of 8a in 130 ml of THF and 1,300 ml of DMF are stirred with 175 g (2.01 mol) of manganese(IV) oxide at room temperature for 48 hours and then the manganese oxide is removed by filtration through a Seitz filter with suction, and the filtrate is evaporated to dryness. The residue is stirred vigorously in petroleum ether, filtered with suction, washed with petroleum ether and dried at 60° C. in vacuo.

Yield: 37.3 g (89%).

$C_8H_6N_2O$ (146.1).

NMR (DMSO): δ=7.78 (d, 2H), 8.22 (s, 1H), 8.52 (s, 1H), 10.05 (s, 1H) ppm.

(c)

5-(Benzimidazol-5(6)-yl)-2,4-imidazolidinedione (8c)

45.8 g (0.313 mol) of 8b in ethanol/water are stirred with 23.03 g (0.47 mol) of sodium cyanide and 120.3 g (1.25 mol) of ammonium carbonate at 60° C. for 20 hours in analogy to Example 1c.

Yield: 36.4 g (54%).

$C_{10}H_8N_4O_2$ (216.2).

NMR (DMSO): δ=5.44 (s, 1H), 7.53 (d, J=9 Hz, 1H), 7.83 (s, 1H), 7.88 (d, J=9 Hz, 1H), 8.63 (s, 1H), 9.63 (s, 1H), 10.93 (s, 1H) ppm.

(d)

DL-α-Amino-α-(benzimidazol-5(6)-acetic acid (DL-benzimidazol-5(6)-ylglycine (8d))

20 g (0.093 mol) of 8c and 105.7 g (0.335 mol, 3.6 equivalents) of barium hydroxide in 1,000 ml of water are stirred at 100° C. for 24 hours. The suspension is then diluted with 500 ml of $H_2O$, and $CO_2$ is passed in at 100° C. for 2 hours, and the precipitated barium carbonate is filtered off while hot with suction and is washed with boiling water. The filtrate is evaporated to dryness.

Yield: 20.1 g (80%).

$C_9H_9N_3O_2.2H_2O.\frac{1}{2}BaCO_3$ (293.0). calculated: C 38.26, H 3.10, N 14.34, Ba 15.62. found: C 40.6, H 3.9, N 15.5, Ba 14.7.

NMR (DCOOD): δ=5.71 (s, 1H), 7.94 (d, 1H), 8.16 (d, 1H), 8.86 (s, 1H) 9.5 (s, 1H) ppm.

(e)

DL-α-t-Butyloxycarbonylamino-α-(1-t-butyloxycarbonylbenzimidazol-5(6)-yl)acetic acid (8e)

12 g (0.044 mol) of 8d are stirred with 38.4 g (0.176 mol) of di-t-butyl dicarbonate at room temperature overnight in analogy to Example 1e. The crude product is dissolved in 80 ml of ethyl acetate and stirred into 600 ml of petroleum ether.

Yield: 14.6 g (84%).

$C_{19}H_{25}N_3O_6$ (391.4): calculated: C 58.30, H. 6.44, N 10.73. found: C 56.8, H 6.6, N 9.8.

NMR (NaOD): δ=1.24 (s, 9H), 1.4 (s, 9H), 5.05 (s, 1H), 7.2 (d, 1H), 7.65 (s and d, 2H), 8.06 (s, 1H), ppm.

(f)

DL-7-(Benzimidazol-5(6)-ylglycylamido)-3-chloro-3-cephem-4-carboxylic acid.trifluoroacetate (8f)

2.0 g (5.1 mmol) of 8e are reacted with 0.71 ml (5.1 mmol) of triethylamine, 0.628 ml (0.51 mmol) of pivaloyl chloride and 1.32 g (5.61 mmol) of 7-ACCA in analogy to Example 1f. 2.3 g (3.78 mmol) of Boc-protected cephalosporin are deblocked in analogy to Example 1g. The trifluoroacetate is dissolved in $H_2O$, and the aqueous phase is washed twice with ethyl acetate/ether (1:1) and freeze-dried.

Yield: 1.5 g (76%).

$C_{16}H_{14}ClN_5O_4S.CF_3COOH$ (521.9).

NMR (DCOOD): δ=3.5–4.03 (mm, 2H), 5.29–5.38 (dd, 1H), 5.88–5.96 (dd and s, 2H), 7.93–8.0 (t, 1H), 8.16–8.22 (t, 1H), 8.3 (s, 1H), 9.52 (m, 1H) ppm.

EXAMPLE 9

D-7-(Benzimidazol-5(6)-ylglycylamido)-3-chloro-cephem-4-carboxyic acid (9a) and L-form (9b)

700 mg of 8f are separated into the D- and L-forms on a preparative HPLC column (Hibar 250-25, RP-18, 7 μm, 220 nm, eluting agent: 1,000 ml $H_2O$-5 ml acetonitrile-1 ml acetic acid). 30 mg portions of the DL mixture 8f are dissolved in 2 ml of the eluting system, applied to the column and separated into 2 fractions (peak I and peak II) at a flow rate of eluting agent of 10 ml/min.

(a) D-form (peak II):

Yield: 18 mg.

Analytical HPLC: see L-form.

Rentention: 8.14.

(b) L-form (peak I)

Yield 42 mg.

Analytical HPLC: (Hibar 250-4, RP-8, 10 μm, 255 nm, mobile phase: 975 ml Merck phosphate buffer pH 7/25 ml acetonitrile, flow rate: 1.5 ml/min).

Retention: 6.90.

NMR (DCOOD): δ=3.74 (d, J=18.5 Hz, 1H), 3.98 (d, J=18.5 Hz, 1H), 5.35 (d, J=5 Hz, 1H), 5.86 (s and d, 2H), 7.96 (d, 1H), 8.16 (d, 1H), 9.5 (s, 1H) ppm.

EXAMPLE 10

DL-7-(Benzimidazol-5(6)-ylglycylamido)-3-methyl-3-cephem-4-carboxylic acid

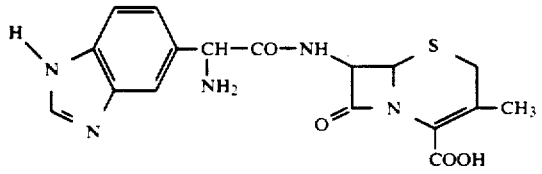

3.5 g (8.9 mmol) of 8e and 1.36 g (8.9 mmol) of 1-hydroxybenzotriazole are dissolved in 15 ml of THF under nitrogen. 1.84 g (8.9 mmol) of N,N'-dicyclohexylcarbodiimide (DCC), dissolved in 10 ml of THF, are added at 10° C., and the mixture is stirred at room temperature for 2 hours. After addition of 2.41 g (8.9 mmol) of t-butyl 7-amino-3-methyl-3-cephem-4-carboxylate, dissolved in 10 ml of $CH_2Cl_2$, the mixture is subsequently stirred overnight without cooling. The precipitated urea is filtered off with suction, washed with THF, and the filtrate is evaporated to dryness. The residue is dissolved in ethyl acetate, and the solution is washed with $NaHCO_3$ solution/water and dried over $Na_2SO_4$, and the filtrate is evaporated to dryness in vacuo (yield 3.7 g ). After chromatography on silica gel with petroleum ether/ethyl acetate (3:1) and petroleum ether/ethyl acetate (1:1), 1.3 g of pure product (23%) are obtained.

1.0 g (1.55 mmol) of Boc-protected cephalosporin are deblocked in analogy to Exaple 3 and TFA is removed on Amberlite IRA-68 (acetate form) and the solution is freeze-dried.

Yield: 260 mg (43%).

$C_{17}H_{17}N_5O_4S$ (387.4).

NMR (DCOOD): δ=2.18 (s, 3H), 3.2-3.65 (mm, 2H), 5.18-5.25 (dd, 1H), 5.78-5.88 (dd, 2H), 7.98 (d, 1H), 8.18 (t, 1H), 9.5 (d, 1H) ppm.

EXAMPLE 11

DL-7-(2-Amino-1H-benzimidazol-5(6)-ylglycylamido)-3-chloro-3-cephem-4-carboxylic acid

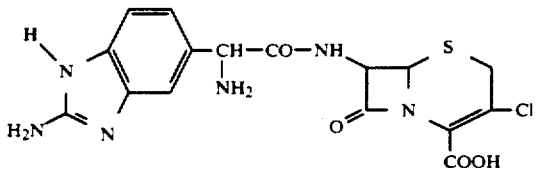

(a)

2-Amino-5(6)-hydroxymethylbenzimidazole (11a)

132 g (0.745 mol) of methyl 2-amino-5(6)-benzimidazolecarboxylate are suspended in 2,200 ml of THF under nitrogen. While cooling slightly (ice bath), 596 ml (2.08 mol) of sodium bis(2-methoxyethoxy)aluminum hydride (Red-Al, 3.5 molar solution in toluene), dissolved in 1,000 ml of THF, are added dropwise at 25°-31° C. within 2 hours. The solution is then stirred without cooling for 1 hour and heated under reflux overnight. The excess Red-Al is cautiously decomposed by addition of 160 ml of water under a stream of nitrogen, and the mixture is then stirred for 1 hour, the aluminium hydroxide is filtered off with suction, washed with 2 l of THF, and the filtrate is evaporated to a dark oil. The residue is taken up in 500 ml of ethyl acetate and the solution is washed three times with 500 ml of water each time. The combined $H_2O$ phases are washed three times with 200 ml of ethyl acetate each time, and the aqueous phase is filtered and freeze-dried.

Yield: 74 g (61%).

$C_8H_9N_3O$ (163.2).

NMR (DMSO): δ=4.46 (s, 2H), 6.24 (s, 2H), 6.82 (d, 1H), 7.03 (d, 1H), 7.09 (s, 1H) ppm.

(b)

2-Aminobenzimidazol-5(6) carboxaldehyde (11b )

74 g (0.453 mol) of 11a in 2,000 ml of glacial acetic acid are stirred with 248.4 g (2.857 mol, 6.3-fold excess) of $MnO_2$ at room temperature for 3 days. The manganese oxide is filtered off with suction, the filtrate is filtered once more through silica gel, and the acetic acid solution is evaporated. The remaining oil is digested in 1.5 l of ethyl acetate, whereupon crystallization occurs. The crystals are filtered off with suction, washed with ether and dried in vacuo.

Yield: 119.7 g (96%).

$C_{10}H_{11}N_3O_3.3H_2O.CH_3COOH$ (275. 3): calculated: C 43.6, H 6.22, N 15.26. found: C 44.2, H 4.9, N 11.0.

(c)

5-(2-Amino-1H-benzimidazol-5-yl)-2,4-imidazolidinedione (11c)

119.7 g (0.435 mol) of 11b in 900 ml of ethanol are stirred with 219 g (2.28 mol) of ammonium carbonate and 41.4 g (0.845 mol) of sodium cyanide in 900 ml of $H_2O$ at 60° C. for 20 hours in analogy to Example 1c. After removal of ethanol by disillation, the suspension is acidified to pH 2 at 0° C., and then the pH is returned to 6.0, whereupon an oily product results and gradually solidifies.

Yield: 57.6 (58%).

$C_{10}H_8N_5O_2$ (231.2): calculated: C 51.94, H 3.92, N 30.28. found: C 51.4, H 4.1, N 29.1.

(d)

DL-α-t-Butyloxycarbonylamino-α-(2-t-butyloxycarbonyl-1H-benzimidazol-5-yl)acetic acid (11d)

41.2 g (0.178 mol) of 11c are stirred with 42.6 g (1.781 mol) of lithium hydroxide in 1,000 ml of $H_2O$ at 100° C. for 2 days in analogy in Example 1d. The solution is filtered hot, the filtrate is acidified to pH 2 at 0° C., and the aqueous phase is extracted with ethyl acetate. The aqueous solution is evaporated to dryness in vacuo.

Yield: 62.4 g.

NMR (NaOD, DMSO): $\delta = 4.12$ (s, 1H), 6.71 (d, 1H), 6.97 (d, 1H), 7.01 (s, 1H) ppm.

The residue is induced to dissolve in 300 ml of water with 25.4 g (0.303 mol) of $NaHCO_3$, and 66.1 g (0.303 mol) of di-t-butyl dicarbonate are added dropwise. The mixture is stirred at room temperature for 2 days. Dioxane is removed by distillation, and the remaining solution is diluted with $H_2O$ and washed with petroleum ether. The aqueous phase is acidified to pH 2.5 with 2N HCl, cooling in ice, and is extracted with ethyl acetate. After washing with sodium chloride solution. Drying over $Na_2SO_4$ and evaporation of the organic phase, 17.9 g of crude product are obtained, and this is reprecipitated from THF/petroleum ether.

Yield: 7.0 g.

$C_{19}H_{26}N_4O_6$ (406.4).

NMR (NaOD): $\delta = 1.42$ (s, 9H), 1.46 (s, 9H), 6.98 (d, 1H), 7.28 (d, 2H) ppm.

(e)

DL-7-(2-Amino-1H-benzimidazol-5-ylglycylamido)-3-chloro-3-cephem-4-carboxylic acid (11e)

4.9 g (12.1 mmol) of 11d are reacted with 1.69 ml (12.1 mmol) of triethylamine, 1.49 ml (12.1 mmol) of pivaloyl chloride and 2.98 g (12.7 mmol) of 7-ACCA in analogy to Example 1f.

Yield: 3.0 g (40%; THF/petroleum ether).

The Boc-protected cephalosporin is treated with TFA/$CH_2Cl_2$ (1:1) in analogy to Example 1g.

Yield: 2.35 g (91%).

$C_{16}H_{15}ClN_6O_4S.CF_3COOH$ (536.9).

NMR (DCOOD): $\delta = 3.52$–4.0 (mm, 2H), 5.28–5.36 (dd, 1H), 5.70 (d, 1H), 5.84–5.92 (dd, 1H), 7.58–7.66 (m, 2H), 7.76 (d, 1H) ppm.

EXAMPLE 12

D-7-(2-Amino-1H-benzimidazol-5-ylglycylamido)-3-chloro-3-cephem-4-carboxylic acid (12a) and L-form (12b)

Preparative HPLC separation of 11e:

Column: Hibar 250-25 (RP-18, 7 μm, 254 nm)

Eluting agent: 1,000 ml $H_2O$-60 ml acetonitrile-1 ml TFA

Amount applied: 2.3 g; 200 mg portions dissolved in 2–3 ml of eluting agent for each passage through the column.

Yield:

Peak I (L-form): 430 mg.

Peak II (D-form): 220 mg.

220 mg of peak II are dissolved in 15 ml of $H_2O$, and the solution is applied to a column containing Amberlite IRA-68 (acetate form), which is washed with 200 ml of $H_2O$. The filtrate is filtered through Millex-GS (0.22 μm) with a syringe, and is then freeze-dried.

Yield: 155 mg.

NMR (DCOOD): $\delta = 3.54$ (d, J = 18 Hz, 1H), 3.86 (d, J = 18 Hz, 1H), 5.28 (d, J = 5 Hz, 1H), 5.68 (s, 1H), 5.92 (d, J = 5 Hz, 1H), 7.58 (d, 1H), 7.66 (d, 1H), 7.76 (s, 1H) ppm.

EXAMPLE 13

DL-7-(2-Amino-1H-benzimidazol-5-ylglycylamido)-3-methyl-3-cephem-4-carboxylic acid

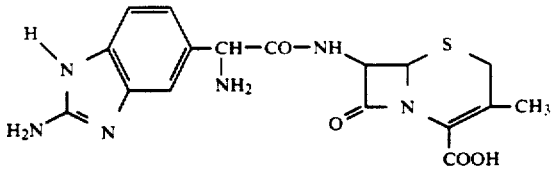

4.0 g (9.84 mmol) of 11d are reacted with 1.71 ml (9.84 mmol) of ethyldiisopropylamine, 0.76 ml (9.84 mmol) of methanesulphonyl chloride and 2.7 g (9.84 mmol) of the t-butyl 7-amino-3-methyl-3-cephem-4-carboxylate in analogy to Example 3. 3.0 g are obtained, and this is purified by chromatography on silica gel (eluting agent: petroleum ether/ethyl acetate 1:1).

Yield: 0.9 g.

0.8 g of Boc-protected cephalosporin are treated with TFA and then with Amberlite IRA-68 (acetate form) in analogy to Example 3.

Yield: 420 mg $C_{17}H_{18}N_6O_4S.2\frac{1}{2}H_2O$ (447.5): calculated: C 45.63, H 5.18, N 18.78, S 7.16. found: C 45.5, H 5.0, N 16.9, S 6.6.

NMR (DCOOD): $\delta = 2.2$ (s, 3H), 3.28–3.69 (mm, 2H), 5.21–5.3 (dd, 1H), 5.75 (d, 1H), 5.82–5.89 (dd, 1H), 7.62–7.74 (m, 2H), 7.82 (s, 1H) ppm.

EXAMPLE 14

DL-7-(2-Trifluoromethyl-1H-benzimidazol-5-ylglycylamido)-3-chloro-3-cephem-4-carboxylic acid

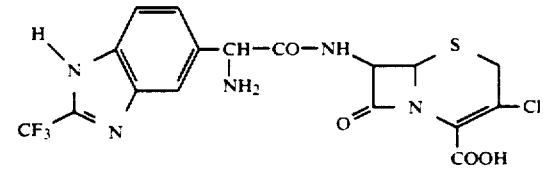

(a)

2-Trifluoromethyl-1H-benzimidazole-5-carboxylic acid (14a)

50 g (0.329 mol) of 3,4-diaminobenzoic acid, dissolved in 300 ml of 4N HCl, are heated under reflux with 40.5 g (0.355 mol) of TFA for 5 hours. The solution is then cooled to 0° C., and the precipitated product is filtered off with suction, washed with water and dried at 40° C. in vacuo.

Yield: 59.7 g (73%).

$C_9H_5F_3N_2O_2.H_2O$ (248.2): calculated: C 43.56, H 2.84, N 11.28, F 22.98. found: C 42.6, H 2.8, N 10.9, F 22.0.

(b)

Methyl 2-trifluoromethyl-1H-benzimidazole-5-carboxylate (14b)

Gaseous hydrogen chloride is passed through a solution of 59.7 g (0.241 mol) of 14a in 1,000 ml of methanol for 2 hours, simultaneously boiling under reflux. The methanol is then removed by distillation, and the residue is dissolved in ethyl acetate/water and the pH is adjusted to 7 with 2N solution hydroxide solution. The ethyl acetate phase is separated off, the aqueous phase is extracted twice with ethyl acetate, and the organic phase is washed with sodium chloride solution, dried over $Na_2SO_4$ and evaporated.

Yield: 54.2 g (92%)

$C_{10}H_7N_2O_2F_3$ (244.2): calculated: C 49.19, H 2.89, N 11.47, F 23.34. found: C 49.6, H 3.1, N 11.3, F 22.4.

NMR (DMSO): δ=4.9 (s, 3H), 7.82 (d, 1H), 8.0 (dd, 1H), 8.30 (s, 1H) ppm.

(c)

2-Trifluoromethyl-5-hydroxymethyl-1H-benzimidazole (14c) 53.4 g (0.219 mol) of 14b in 600 ml of THF are stirred with 728.9 ml (0.875 mol) of DIBAL (20% strength solution in toluene at −70° C. overnight in analogy to Example 1a.

Crude yield 45.4 g $C_9H_7F_3N_2O$ (216.2): calculated: C 50.0, H 3.26, N 12.96, F 26.37. found: C 49.7, H 3.7, N 11.7, F 26.0.

After chromatography on silica gel 60 (Merck, 0.04–0.063 mm) using the eluting agent toluene/ethyl acetate (3:1), toluene/ethyl acetate (1:1), toluene/ethyl acetate (1:3) and ethyl acetate, 29.3 g (62%) of benzimidazole alcohol are obtained.

NMR (DMSO): δ=4.64 (s, 2H), 5.32 (broad s, 1H), 7.36 (d, 1H), 7.66 (s, 1H), 7.71 (d 1H) ppm.

(d)

2-Trifluoromethyl-1H-benzimidazole-5-carboxaldehyde (14d)

29.3 g (0.136 mol) of 14c in 1,000 ml of THF are stirred with 71.4 g (0.821 mol) of manganese(IV) oxide at room temperature for 48 hours in analogy to Example 1b.

Yield: 23.8 g (82%).

$C_9H_5F_3N_2O$ (214.2).

NMR (DMSO): δ=7.87 (q, 2H), 8.32 (s, 1H), 10.11 (s, 1H) ppm.

(e)

5-(2-Trifluoromethyl-1H-benzimidazol-5-yl)-2,4-imidazolidinedione (14e)

29.2 g (0.136 mol) of 14d in ethanol/water are reacted with 55 g (0.573 mol) of ammonium carbonate and 10.4 g (0.212 mol) of sodium cynanide in analogy to Example 1c. After removal of ethanol by distillation, the solution is acidified with 2N HCl to pH 2 at 0° C., then the pH is returned to 4.5 and the solution is extracted several times with ethyl acetate. The combined ethyl acetate phases are washed with sodium chloride solution, dried and evaporated.

Yield: 31.2 g (80.6%).

$C_{11}H_7F_3N_4O_2$ (284.2).

NMR (DMSO): δ=5.85 (s, 1H), 7.34 (d, 1H), 7.69 (s, 1H), 7.77 (d, 1H), 8.5 (s, 1H), 10.83 (s, 1H) ppm.

(f)

DL-α-Amino-α-(2-trifluoromethyl-1H-benzimidazol-5-yl)acetic acid (14f)

35.7 g (0.126 mol) of 14e are cleaved with 500 ml of hydrobromic acid (48%) in analogy to Example 5e.

Yield: 18.1 g (42%).

$C_{10}H_8F_3N_3O_2.HBr$ (340.0).

NMR (DCOOD): δ=5.88 (s, 1H), 8.1 (d, 1H), 8.28 (d, 1H), 8.46 (s, 1H) ppm.

(g)

DL-α-t-Butyloxycarbonylamino-α-(2-trifluoromethyl-1H-benzimidazol-5-yl)acetic acid (14g)

23.6 g (0.069 mol) of 14f are dissolved in 150 ml of 10% $NaHCO_3$ solution and in 150 ml of dioxane, and 48.2 g (0.221 mol) of di-t-butyl dicarbonate are added and the mixture is stirred at room temperature overnight. Dioxane is removed by distillation, and the aqueous phase is extracted with petroleum ether and acidified with 2N HCl to pH 2 at 0° C. in the presence of ethyl acetate. The ethyl acetate phase is separated off, washed with sodium chloride solution, dried over $Na_2SO_4$ and evaporated. The crude product is dissolved in ether, some insolubles are filtered off, and the solution is stirred into petroleum ether and the product is filtered off with suction.

Yield: 10.8 g (43%)

$C_{15}H_{16}F_3N_3O_4$ (359.3): calculated: C 50.14, H 4.49, N 11.69, F 15.86. found: C 50.1, H 4.8, N 12.4, F 15.1.

(h)

DL-7-(2-Trifluoromethyl-1H-benzimidazol-5-ylglycylamido)-3-chloro-3-cephem-4-carboxylic acid (14h)

4.0 g (11.1 mmol) of 14g are reacted with 1.56 ml (11.1 mmol) of triethylamine, 1.4 ml (11.1 mmol) of pivaloyl chloride and 2.92 g (12.4 mmol) of 7-ACCA in analogy to Example 1f.

Yield: 5.1 g (89%)

In analogy to Example 1g, the Boc-protected cephalosporin is deblocked and converted into the betaine.

Yield: 2.0 g (36%).

$C_{17}H_{13}ClF_3N_5O_4S.1\frac{1}{2}H_2O$ (502.9): calculated: C 40.61, H 3.20, N 13.93, S 6.37, F 11.34. found: C 40.2, H 3.6, N 13.6, S 4.8, F 12.2.

EXAMPLE 15

D-7-(2-Trifluoromethyl-1H-benzimidazol-5-ylglycylamido)-3-chloro-3-cephem-4-carboxylic acid (15a) and L-form (15b)

Preparative HPLC separation of 14h

Column: Hibar 250-25 (RP-18, 7 μm, 254 nm).

Eluting agent: 2,500 ml $H_2O$—250 ml acetonitrile—2.5 ml TFA.

Flow rate: 10 ml/min.

L-form (peak I):

1.4 g of 14h are suspended in 20 ml of eluting agent, whereupon 400 mg of insoluble material is left behind as the pure L-form.

NMR (DCOOD): δ=3.7 (d, 1H), 3.93 (d, 1H), 5.3 (d, 1H), 5.78 (s, and d, 2H), 7.8 (d, 1H), 8.05 (d, 1H), 8.23 (s, 1H) ppm.

D-form (peak II):

The filtrate is filtered through a Millex filter with a syringe and is pumped onto the column at 0.5 ml/min. The eluate is freeze-dried.

Yield: 300 mg

NMR (DCOOD): δ=3.5 (d, J=18.5 Hz, 1H), 3.85 (d, J=18.5 Hz, 1H), 5.25 (d, J=5 Hz, 1H), 5.78 (s, 1H), 5.9 (d, J=5 Hz, 1H), 7.78 (d, 1H), 8.06 (d, 1H), 8.21 (s, 1H) ppm.

EXAMPLE 16

DL-6-(2-Trifluoromethyl-1H-benzimidazol-5-ylglycylamido)penicillanic acid

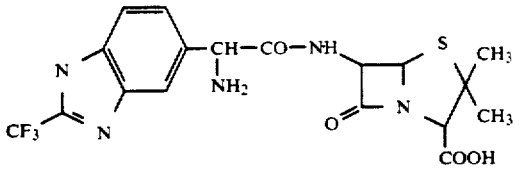

(a)

DL-α-Benzyloxycarbonylamino-α-(2-trifluoromethyl-1H-benzimidazol-5-yl)acetic acid (16a)

9.2 g (27.1 mmol) of 14f are dissolved in 50 ml of water, and the pH is adjusted to 9 with 2N sodium hydroxide solution. The clear solution is cooled to 0°-5° C., and 8.1 ml (0.0569 mol) of benzyl chloroformate are added dropwise within 30 minutes, with simultaneous addition of 2N sodium hydroxide solution (pH range 8-10). After stirring at room temperature for 50 minutes, the mixture is extracted once with ether/ethyl acetate (1:1), and the aqueous phase is acidified to pH 2 with 2N HCl and is extracted with ethyl acetate. After washing with water and drying over $Na_2SO_4$, the residue is reprecipitated from ethyl acetate/petroleum ether.

Yield: 2.8 g (26%).

$C_{18}H_{14}F_3N_3O_4$ (393.3).

NMR (DMSO): δ=5.09 (t, 2H), 5.38 (d, 1H), 7.34 (m, 5H), 7.47 (d, 1H), 7.73 (d, 1H), 7.78 (s, 1H), 8.23 (d, 1H) ppm.

(b)

Allyl DL-6-[α-benzyloxycarbonylamino-α-(2-trifluoromethyl-1H-benzimidazol-5-ylglycylamido)]penicillanate (16b)

2.6 g (6.61 mmol) of 16a are reacted with 1.15 ml (6.61 mmol) of ethyldiisopropylamine, 0.512 ml (6.61 mmol) of methanesulphonyl chloride and a solution of 3.0 g (6.95 mmol) of the p-toluenesulphonic acid salt of allyl 6-aminopenicillanate and 1.21 ml (6.95 mmol) of ethyldiisopropylamine in THF/DMF in analogy to Example 6b.

Yield: 3.5 g (83%).

$C_{29}H_{28}F_3N_5O_6S$ (631.6).

(c)

Sodium DL-6-(2-trifluoromethyl-1H-benzimidazol-5-yl-glyclyamido)penicillanate (16c)

3.5 g (5.54 mmol) of 16b are deacylated by hydrogenolysis in analogy to Example 6d. 1.8 g (3.62 mmol) of allyl ester are treated with 10.7 ml (5.43 mmol) of 0.5 m sodium caprylate, 95 mg (0.363 mmol) of triphenylphosphine and 96.2 mg (0.083 mmol) of tetrakis(triphenylphosphine)palladim(O) in THF under nitrogen in analogy to Example 4c.

Yield: 1.1 g (65%).

$C_{18}H_{17}F_3N_5O_4SNa$ (479.4).

MNR (DMSO): δ=1.43-1.58 (m, 6H), 3.91 (d, 1H), 4.53 (d, 1H), 5.33-5.44 (m, 2H), 7.05 (m, 1H), 7.38 (d, 1H), 7.5 (s, 1H) ppm.

EXAMPLE 17

D-6-(2-Trifluoromethyl-1H-benzimidazol-5-ylglycylamido)penicillanic acid (17a) and L-form (17b)

700 mg of 16c are dissolved in 10 ml of eluting agent on a preparative Hibar column (Merck 250-25, 7 μm, 254 nm, eluting agent: 2250 ml water—125 ml acetonitrile—125 ml acetic acid), pumped onto the column and separated into the D- and L-forms.

L-form (peak I):

Yield: 110 mg $C_{18}H_{18}F_3N_5O_4S.2H_2O.\frac{1}{3}CH_3COOH$ (513.5): calculated: C 42.10, H 4.58, N 13.64. found: C 41.2, H 4.7, N 12.1.

NMR (DMSO): δ=1.47 (s, 3H), 1.58 (s, 3H), 4.14 (s, 1H), 4.9 (s, 1H), 5.48 (t, 2H), 7.47 (d, 1H), 7.74 (d, 1H), 7.82 (s, 1H) ppm.

Analytical HPLC: Hibar 250-4, RP-8, 10 μm, 254 nm, eluting agent: 900 ml $H_2O$-50 ml acetonitrile-50 ml acetic acid, flow rate: 3 ml/min, 1 mg/ml, Retention: 6.2 (purity: 86.6%).

D-form (peak II):

Yield: 129 mg.

NMR (DMSO): δ=1.38 (s, 3H), 1.5 (s, 3H), 4.1 (s, 1H), 4.95 (s, 1H), 5.39 (d, J=4 Hz, 1H), 5.5 (s, 1H), 7.48 (d, 1H), 7.74 (d, 1H), 7.82 (s, 1H) ppm.

Analytical HPLC: compare the L-form.

Retention: 9.11 (purity: 93.5%).

EXAMPLE 18

DL-7-(2-Methyl-1H-benzimidazol-5-ylglycylamido)-3-chloro-3-cephem-4-carboxylic acid

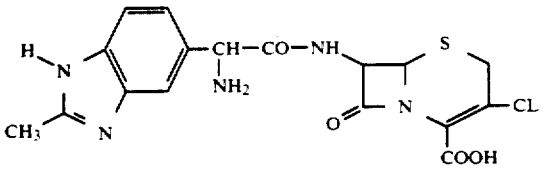

(a)

2-Methyl-1H-benzimidazole-5-carboxylic acid (18a)

100 g (0.657 mol) of 3,4-diaminobenzoic acid are boiled under reflux with 47.3 g (0.788 mol) of glacial acetic acid and 600 ml of 4N HCl in analogy to Example 14a.

Yield: 108.5 g (72%)

$C_9H_8N_2O_2.3H_2O$ (230.2): calculated: C 46.59, H 6.13, N 12.17. found: C 46.7, H 4.0, N 12.2.

(b)

Methyl 2-methyl-1H-benzimidazole-5-carboxylate (18b)

46.6 g (0.202 mol) of 18a are reacted with methanol and gaseous hydrogen chloride in analogy to Example 14b.

Yield: 31.2 g (81%).

$C_{10}H_{10}N_2O_2$ (190.2): calculated: C 63.18, H 5.30, N 14.73. found: C 63.1, H 5.3, N 14.6.

(c)

2-Methyl-5-hydroxymethyl-1H-benzimidazole (18c)

27.8 g (0.146 mol) of 18b in 500 ml of THF are treated with 365.4 ml (0.438 mol) of DIBAL (20% strength solution in toluene) at −70° C. overnight in analogy to Example 1a. The crude product is vigorously stirred in boiling ethyl acetate and, after cooling to 20° C., the remaining material is filtered off with suction.

Yield: 10.2 g (43%).

$C_9H_{10}N_2O$ (162.2).

NMR (DMSO): δ=2.51 (s, 3H), 4.55 (s, 2H), 7.06 (d, 1H), 7.38 (s and d, 2H) ppm.

(d)

2-Methyl-1H-benzimidazole-5-carboxaldehyde (18d)

24.4 g (0.15 mol) of 18c in 400 ml of DMF are stirred with 84.8 g (0.975 mol) of manganese(IV) oxide at room temperature for 3 days in analogy to Example 8b.

Yield: 13.9 g (58%).

$C_9H_8N_2O$ (160.2).

NMR (DMSO): δ=2.56 (s, 3H), 7.61 (d, 1H), 7.71 (d, 1H), 8.06 (s, 1H), 10.02 (s, 1H) ppm.

(e)

DL-α-Amino-α-(2-methyl-1H-benzimidazol-5-yl)acetic acid (18e)

22.7 g (0.142 mol) of 18d are reacted with 57.2 g (0.596 mol) of ammonium carbonate and 10.8 g (0.22 mol) of sodium cyanide in ethanol/water at 60° C. for 20 hours in analogy to Example 1c.

After removal of ethanol by distillation, the solution is acidified to pH 2 with 2N HCl, and then the pH is returned to 4.5 with 2N sodium hydroxide solution. The clear solution is extracted twice with ethyl acetate, and the aqueous phase is evaporated to dryness in vacuo.

Yield: 49.0 (contains NaCl)

All the material is cleaved with 500 ml of hydrobromic acid (48%) in analogy to Example 3c.

Yield: 56.8 g.

$C_{10}H_{11}N_3O_2.2HBr$ (367.1).

NMR (DCOOD): δ=5.82 (s, 1H), 7.88 (d, 1H), 8.05 (d, 1H), 8.22 (s, 1H) ppm.

(f)

DL-α-t-Butyloxycarbonylamino-α-(1-t-butyloxycarbonyl-2-methylbenzimidazol-5-yl)acetic acid (18f)

63.1 g (0.172 mol) of 18e in $NaHCO_3$ solution and dioxane are reacted with 112.6 g (0.516 mol) of di-t-butyl dicarbonate in analogy to Example 14g.

Yield: 12.6 g.

$C_{20}H_{27}N_3O_6$ (405.4).

NMR (DMSO): δ=13.5 (d, 9H), 1.65 (d, 9H), 5.22 (q, 1H), 7.36 (m, 1H), 7.65 (m, 1H), 7.96 (d, 1H) ppm.

(g)

DL-7-(2-Methyl-1H-benzimidazol-5-ylglycylamido)-3-chloro-3-cephem-4-carboxylic acid (18g)

4.2 g (10.3 mmol) of 18f are reacted with 1.44 ml (10.3 mmol) of triethylamine, 1.27 ml (10.3 mmol) of pivaloyl chloride and 2.65 g (11.4 mmol) of 7-ACCA in analogy to Example 1f.

Yield: 4.6 g (72%).

$C_{27}H_{32}ClN_5O_8S$ (622.1).

4.0 g (6.43 mmol) of Boc-protected cephalosporin are deacylated in analogy to Example 1g.

Yield: 2.9 g (85%).

$C_{17}H_{16}ClN_5O_4S.CF_3COOH$ (535.9).

NMR (DCOOD): δ=3.02 (s, 3H), 3.48–4.0 (mm, 2H), 5.27–5.36 (dd, 1H), 5.82 (s, 1H), 5.84–5.94 (dd, 1H), 7.86 (d, 1H), 8.02 (d, 1H) 8.16 (s, 1H) ppm.

EXAMPLE 19

D-7-(2-Methyl-1H-benzimidazol-5-ylglycylamido)-3-chloro-3-cephem-4-carboxylic acid (19a) and L-form (19b)

Preparative HPLC separation of 18g:

Column: Whatman Partisil-10, 500×22 mm, 10 μm (Magnum 20 CCS-RP-8), 254 nm.

Eluting agent: 2500 ml $H_2O$-2.5 ml TFA.

Flow rate: 15 ml/min (chart speed 5 min/min).

Amount applied: 1100 mg of 18 g in 9 ml of eluting agent, filtered through Millex GS, 0.22 μm.

L-form (peak I):

Yield: 355 mg (trifluoroacetate).

NMR (DCOOD): δ=3.06 (s, 3H), 3.75 (d, J=18 Hz, 1H), 3.98 (d, J=18 Hz, 1H), 5.37 (d, J=5 Hz, 1H), 5.84 (s, 1H), 5.88 (d, J=5 Hz, 1H), 7.88 (d, J=9 Hz, 1H), 8.04 (d, J=9 Hz, 1H), 8.18 (s, 1H) ppm.

D-form (peak II):

Yield: 114 mg (trifluoroacetate).

NMR (OCOOD): δ=3.04 (s, 3H), 3.54 (d, J=18 Hz, 1H), 3.87 (d, J=18 Hz, 1H), 5.29 (d, J=5 Hz, 1H), 5.82 (s, 1H), 5.94 (d, J=5 Hz, 1H), 7.86 (dd, 1H), 8.04 (d, 1H), 8.16 (s, 1H) ppm.

EXAMPLE 20

DL-7-(2,3-Dihydro-2-oxo-1H-benzimidazol-5-ylglycylamido)-3-chloro-3-cephem-4-carboxylic acid

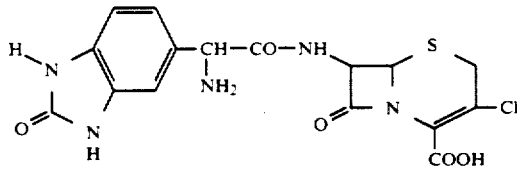

(a)

Methyl 2,3-dihydro-2-oxo-1H-benzimidazole-5-carboxylate (20a)

20 g (0.12 mol) of methyl 3,4-diaminobenzoate and 24.8 g (0.12 mol) of N,N'-dicarbomethoxy-S-methylisothiourea in 180 ml of DMF are heated under reflux for 4 hours. The DMF is then removed by distillation, the residue is vigorously stirred with water, and the crystals which have separated out are filtered off with suction and washed with water. After drying of the substance at 40° C. in vacuo, the product is suspended in acetone and then filtered off with suction.

Yield: 21.9 g (95%).

$C_9H_8N_2O_3$ (192.2).

NMR (DMSO): δ=3.8 (s, 3H), 7.01 (d, 1H), 7.48 (s, 1H), 7.64 (d, 1H), 10.9 (s, 1H), 11.08 (s, 1H), ppm.

(b)

2,3-Dihydro-2-oxo-5-hydroxymethyl-1H-benzimidazole (20b)

24.6 g (0.128 mol) of 20a are suspended in THF and stirred with 624.8 ml (0.768 mol) of DIBAL (20% strength solution in toluene) at −70° C. overnight in analogy to Example 1a.

Yield: 16.2 g (77%).

$C_8H_8N_2O_2$ (164.2).

NMR (DMSO): δ=4.48 (s, 2H), 5.12 (broad s, 1H), 6.91 (s, 2H), 6.98 (s, 1H), 10.61 (broad s, 2H) ppm.

(c)

2,3-Dihydro-2-oxo-1H-benzimidazole-5-carboxaldehyde (20c)

25.7 g (0.157 mol) of 20b in DMF are stirred with 81.7 g (0.939 mol) of manganese(IV) oxide for 2 days in analogy to Example 8b.

Yield: 18.5 g (73%).

$C_8H_6N_2O_2$ (162.1).

NMR (DMSO): δ=7.1 (d, J=7.5 Hz, 1H), 7.41 (s, 1H), 7.59 (d, J=7.5 Hz, 1H), 9.44 (s, 1H), 11.02 (s, 1H) 11.20 (s, 1H) ppm.

(d)

5-(2,3-Dihydro-2-oxo-1H-benzimidazol-5-yl)-2,4-imidazolidinedione (20d)

10.7 g (0.0659 mol) of 20c in methanol/water are reacted with 27.8 g (0.289 mol) of ammonium carbonate and 5.2 g (0.107 mol) of sodium cyanide in analogy to Example 1c.

Yield: 10 g (65%).

$C_{10}H_8N_4O_3$ (232.2).

NMR (DMSO): δ=5.11 (s, 1H), 6.85 (s, 1H), 6.9 (weak d, 2H), 8.36 (s, 1H), 10.68 (s, 3H) ppm.

(e)

DL-α-(t-Butyloxycarbonylamino)-α-(2,3-dihydro-2-oxo-1H-benzimidazol-5-ylacetic acid (20e)

8.8 g (0.0379 mol) of 20d are cleaved with 100 ml of hydrobromic acid (48%) in analogy to Example 5e.

Yield: 10 g (79%).

$C_9H_9N_3O_3.HBr$ (336.1).

10 g (29.7 mmol) of amino acid hydrobromide are reacted in 50 ml of 2N sodium hydroxide solution, 50 ml of $H_2O$ and 100 ml of dioxane and 19.4 g (89.1 mmol) of di-t-butyl dicarbonate in analogy to Example 1e.

Yield: 5.4 g (59%).

$C_{14}H_{17}N_3O_5$ (307.3).

NMR (DMSO): δ=1.4 (s, 9H), 5.08 (d, 1H), 6.9 (d, 1H), 6.99 (s and d, 2H), 7.5 (d, 1H), 10.67 (d, 2H) ppm.

(f)

DL-7-(2,3-Dihydro-2-oxo-1H-benzimidazol-5-ylglycylamido)-3-chloro-3-cephem-4-carboxylic acid 1.0 g (3.25 mmol) of 20e is reacted with 0.455 ml (3.25 mmol) of triethylamine, 0.4 ml (3.25 mmol) of pivaloyl chloride and 0.84 g (3.58 mmol) of 7-ACCA in analogy to Example 1f.

Yield: 1.2 g (71%).

$C_{21}H_{22}ClN_5O_7S$ (523.9).

1.1 g (2.1 mmol) of Boc-protected cephalosporin is vigorously stirred in TFA/$CH_2Cl_2$ and converted into the betaine with Amberlite IRA-68 (acetate form) in analogy to Example 1g.

Yield: 340 mg (35%).

$C_{16}H_{14}ClN_5O_5S.2H_2O$ (459.9).

NMR (DCOOD): δ=3.52–4.01 (mm, 2H), 5.25–5.33 (dd, 1H), 5.61 (s, 1H), 5.8–5.9 (dd, 1H), 7.39 (d, 2H), 7.51 (s, 1H) ppm.

EXAMPLE 21

D-7-(2,3-Dihydro-2-oxo-1H-benzimidazol-5-ylglycylamido)-3-chloro-3-cephem-4-carboxylic acid (21a) and L-form (21b)

Preparative HPLC separation of 20f

Column: Hibar 250-25, RP-18, 7 μm, 254 nm.

Eluting agent: 925 ml $H_2O$—75 ml acetonitrile—1 ml TFA.

Amount applied: 310 mg.

L-form (peak I):

Yield: 86 mg (trifluoroacetate).

NMR (DCOOD): δ=3.71 (d, J=18 Hz, 1H), 3.95 (d, J=18 Hz, 1H), 5.31 (d, 1H), 5.61 (s, 1H), 5.82 (d, 1H), 7.38 (s, 2H), 7.5 (s, 1H) ppm.

Analytical HPLC: Hibar 250-4, RP-8, 10 μm, 254 nm,

Eluting agent: 925 ml $H_2O$—75 ml acetonitrile—1 ml TFA,

Flow rate: 1.5 ml/min, 0.5 mg/ml.

Retention: 4.5 (purity 98%).

D-form (peak II):

Yield: 144 mg (trifluoroacetate).

Analytical HPLC: compare L-form.

Retention: 5.34 (purity: 94.5%).

NMR (DCOOD): δ=3.57 (d, 1H), 3.91 (d, 1H), 5.3 (broad s, 1H), 5.63 (broad s, 1H), 5.92 (broad s, 1H), 7.41 (s, 2H), 7.55 (d, 1H) ppm.

EXAMPLE 22

D-7-(2-Aminobenzoxazol-5-ylglycylamido)-3-chloro-3-cephem-4-carboxylic acid

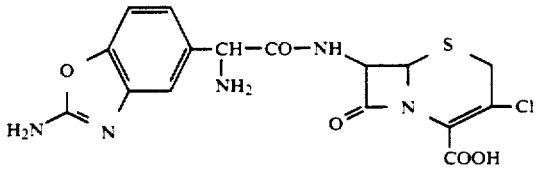

(a)

D-α-t-Butyloxycarbonylamino-α-(3-amino-4-hydroxyphenyl)acetic acid (22a)

A solution of 29.1 g (93.2 mmol) of D-α-butyloxycarbonylamino-α-(3-nitro-4-hydroxyphenyl)acetic acid in 300 ml of $CH_3OH$ is hydrogenated in the presence of 2 g of palladium on active charcoal (10% Pd) under pressure for 3 hours. The hydrogenation mixture is filtered, and solvent is removed in vacuo. The residue is chromatographed on a silica gel column with the following solvent system methylene chloride/methanol (10:1), methylene chloride/methanol (1:1) and methanol.

Yield: 9.8 g (37%).

$C_{13}H_{18}N_2O_5$ (282.3).

NMR (DMSO): δ=1.36 (s, 9H), 4.69 (d, 1H), 6.38 (d, 1H), 6.53–6.58 (s and d, 2H) ppm.

(b)

D-α-t-Butyloxycarbonylamino-α-(2-aminobenzoxazol-5-yl)acetic acid hydrobromide (22b)

5.5 g (19.5 mmol) of 22a are dissolved in 40 ml of methanol and, while stirring, 2.2 g (20.5 mmol) of cyanogen bromide, dissolved in 20 ml of $CH_3OH$, are added dropwise at room temperature, and the mixture is stirred overnight. The reaction mixture is evaporated to dryness in vacuo. The residue is dissolved in THF, and the solution is filtered and stirred into petroleum ether, and the precipitated product is filtered off with suction and dried in vacuo.

Yield: 4.5 g (57%).

$C_{14}H_{17}N_3O_5.HBr.H_2O$ (406.2).

NMR (DMSO): δ=1.36 (s, 9H), 5.18 (d, 1H), 7.19 (d, 1H), 7.34 (s, 1H), 7.47 (d, 1H), 7.66 (d, 1H), 8.98 (broad s, 1H) ppm.

(c)

D-7-(2-Aminobenzoxazol-5-ylglycylamido)-3-chloro-3-cephem-4-carboxylic acid (22c)

4.5 g (11 mmol) of 22 b are reacted with 3.1 ml (22 mmol) of triethylamine, 1.35 ml (11 mmol) of pivaloyl chloride and 2.84 g (12.1 mmol) of 7-ACCA, which is induced to dissolve in 30 ml of THF and 12 ml of $H_2O$ with the addition of 10% strength triethylamine solution in THF, in analogy to Example 1f.

Yield: 2.2 g (38%).

In analogy to Example 1g, 1.3 g (2.5 mmol) of Boc-protected cephalosporin are deblocked and converted into the betaine using Amberlite IRA-68.

Yield: 290 mg.

$C_{16}H_{14}ClN_5O_5S.2H_2O$ (459.9).

The crude product is purified on a preparative HPLC column (Hibar-250-25, RP-18, 7 μm, eluting agent: 1000 ml $H_2O$-5 ml acetic acid).

Yield: 83 mg (purity: 99%).

NMR (DCOOD): δ=3.58 (d, J=18 Hz, 1H), 3.91 (d, J=18 Hz, 1H), 5.31 (d, J=5 Hz, 1H), 5.76 (s, 1H), 5.93 (d, J=5 Hz, 1H), 7.76 (d, J=7.5 Hz, 1H), 7.83–7.88 (s and d, 2H) ppm.

EXAMPLE 23

DL-7-(Benzotriazol-5(6)-ylglycylamido)-3-chloro-3-cephem-4-carboxylic acid

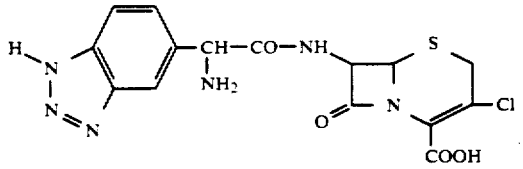

(a)

5(6)-Hydroxymethylbenzotriazole (23a)

55.3 g (0.312 mol) of methyl benzotriazole-5(6)-carboxylate in 1300 ml of THF are reacted with 800 ml (0.936 mol) of DIBAL (20% strength solution in toluene) in analogy to Example 1g.

Yield: 37.2 g (80%).

$C_7H_7N_3O$ (149.2).

NMR (DMSO): δ=4.71 (s, 2H), 7.44 (d, 1H), 7.83 (s, 1H), 7.92 (d, 1H) ppm.

(b)

Benzotriazole-5(6)-carboxyaldehyde (23b)

2.1 g (14.1 mmol) of 23a in 1000 ml of THF are stirred with 8.4 g (96.6 mmol) of manganese(IV) oxide at room temperature for 4 days in analogy to Example 1b.

Yield: 1.4 g (68%)

$C_7H_5N_3O$ (147.1)

NMR (DMSO): δ=8.0–8.1 (dd, 2H), 8.7 (s, 1H), 10.12 (s, 1H), 12.03 (broad s, 1H) ppm.

(c)

5-(Benzotriazol-5(6)-yl)-2,4-imidazolidinedione (23c)

30.9 g (0.21 mol) of 23b in ethanol and water are reacted with 15.9 g (0.325 mol) of sodium cyanide and 84.7 g (0.882 mol) of ammonium carbonate in analogy to Example 1c.

Yield: 30 g (66%).

$C_9H_7N_5O_2$ (217.2). calculated: C 49.77, H 3.25, N 32.24. found: C 49.0, H 3.6, N 31.2.

(d)

DL-α-Amino-α-(benzotriazol-5(6)-yl)acetic acid (23d)

30 g (0.138 mol) of 23c and 161.7 g (0.508 mol) of barium hydroxide in 980 ml of $H_20$ are boiled under reflux for 30 hours in analogy to Example 8d.

Yield: 16.8 g (63%).

$C_8H_8N_4O_2$ (192.2).

NMR (DCOOD): δ=5.76 (s, 1H), 7.86 (dd, 1H), 8.21 (d, 1H), 8.4 (s, 1H) ppm.

(e)

DL-α-t-Butyloxycarbonylamino-α-(benzotriazol-5(6)-yl)-acetic acid (23e)

12 g (62.5 mmol) of 23d are stirred overnight with 34 g (156 mmol) of di-t-butyl dicarbonate in dioxane and 2N sodium hydroxide solution in analogy to Example 1e. Crystallisation from ethyl acetate/ether/petroleum ether.

Yield: 11.9 g (65%).

$C_{13}H_{16}N_4O_4$ (292.3).

NMR (DMSO): δ=1.40 (s, 9H), 5.37 (d, 1H), 7.53 (d, 1H), 7.76 (d, 1H), 7.94 (broad s, 2H) ppm.

(f)

DL-7-(Benzotriazol-5(6)-ylglycylamido)-3-chloro-3-cephem-4-carboxylic acid (23f)

4.0 g (13.7 mmol) of 23e in THF are reacted with 1.85 g (13.7 mmol) of 1-hydroxybenzotriazole, 2.82 g (13.7 mmol) of DCC and 3.22 g (13.7 mmol) of 7-ACCA, which goes into solution in THF with 8.5 ml (34.4 mmol) of N,O-bis-(trimethylsilyl)acetamide, in analogy to Example 10. After removal of dicyclohexylurea by filtration with suction, the filtrate is evaporated to dryness and the residue is dissolved in $H_2O$ at pH 7. After extraction with ethyl acetate, the aqueous solution is adjusted to pH 2.5 with 2N HCl and is extracted twice with ethyl acetate. The organic phase is washed to neutrality, dried over $Na_2SO_4$ and evaporated. The residue is reprecipitated from ethyl acetate/petroleum ether.

Yield: 3.8 g (55%).

$C_{20}H_{21}ClN_6O_6S$ (508.9).

In analogy to Example 1 g, 0.8 g (1.57 mmol) of Boc-protected cephalosporin is deblocked and converted into the betaine.

Yield: 250 mg (36%).

$C_{15}H_{13}ClN_6O_4S.H_2O$ (444.8).

NMR (DCOOD): δ=3.46–3.82 (mm, 2H), 5.25–5.32 (dd, 1H), 5.76–5.92 (dd and s, 2H), 7.87 (d, 1H), 8.22 (d, 1H) 8.92 (s, 1H) ppm.

EXAMPLE 24

D-7-(2-Aminobenzothiazol-5-ylglycylamido)-3-chloro-3-cephem-4-carboxylic acid

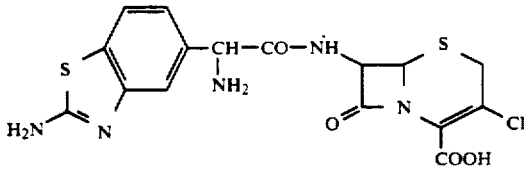

(a)

DL-α-Amino-α-(2-aminobenzothiazol-5-yl)acetic acid (24a)

23.6 g (0.095 mol) of 5-(2-aminobenzothiazol-5-yl)-2,4-imidazolidinedione are cleaved with 22.7 g (0.95 mol) of LiOH—dissolved in 1,000 m of water—in analogy to Example 1d.

Yield: 11.3 g (46%).

$C_9H_9N_3O_2S.2H_2O$ (259.3).

NMR (DMSO): δ=5.71 (s, 1H); 7.96–8.1 (dd, 2H); 8.2 (s, 1H) ppm.

(b)

DL-α-t-Butyloxycarbonylamino-α-(2-aminobenzothiazol-5-yl)acetic acid (24b)

11.3 g (0.0436 mol) of 24a are stirred overnight at room temperature with 14.3 g (0.0654 mol, 1.5 equivalents) of di-t-butyl dicarbonate in analogy to Example 1e. The crude product is recrystallized from THF/petroleum ether.

Yield: 6.5 g (45%).

$C_{14}H_{17}N_3O_4S.\frac{1}{2}H_2O$ (332.4): calculated: C 50.58, H 5.5, N 12.6, S 9.64. found: C 50.0, H 5.2, N 11.2, S 9.2.

NMR (DMSO): δ=1.37 (s, 9H), 5.11 (d, 1H); 7.04 (d, 1H); 7.36 (d, 1H), 7.59 (s, 2H); 7.63 (s, 1H) ppm.

(c)

D-7-(2-Aminobenzothiazol-5-ylglycylamido)-3-chloro-3-cephem-4-carboxylic acid (24c)

1.0 g (3.09 mmol) of 24b is activated with 0.433 ml (3.09 mmol) of triethylamine and 0.38 ml (3.09 mmol) of pivaloyl chloride in 10 ml of DMF, and then reacted with 0.726 g (3.09 mmol) of 7-ACCA which has previously been induced to dissolve in 7 ml of THF, 3.5 ml of water and 2 ml of DMF with triethylamine, in analogy to Example 1f.

The Boc-protected cephalosporin is deacylated in analogy to Example 1g.

Yield: 970 mg (57%).

$C_{16}H_{14}ClN_5O_4S_2.CF_3COOH$ (553.9).

The trifluoroacetate is taken up in the eluting system 1,000 ml water—40 ml acetonitrile—1 ml TFA, a little HP-20 AG adsorber resin (30–60 mesh, Diaion-Mitsubishi) is added, and the mixture is evaporated to a mass of crystals in vacuo. The residue is applied to a column packed with HP-20 and eluted with the above-mentioned eluting system.

Yields:

Peak I (L-form): 115 mg

Peak I/II: 383 mg.

After HPLC chromatography of the mixed fraction (peak I/II) on a Whatman column (Magnum 20, 500×22, 10 μm, CSS-RP-8) using 0.1% TFA/1% acetonitrile in water as the eluting agent, pure D-material (peak II) is obtained and this is then converted into the betaine using Amberlite IRA-68 (acetate form).

Yield: 48 mg (HPLC purity: 94%).

$C_{16}H_{14}ClN_5O_4S_2.3H_2O$ (493.9).

NMR (DCOOD): =3.57 (d, J=18 Hz, 1H), 3.9 (d, J=18 Hz, 1H); 5.3 (d, J=5 Hz, 1H); 5.73 (s, 1H), 5.91 (d, J=5 Hz, 1H), 7.7 (d, 1H), 7.9 (s, 1H), 8.04 (d, 1H) ppm.

It is understood that the specification and examples are illustrative but not limitative of the present invention and that other embodiments within the spirit and scope of the invention will suggest themselves to those skilled in the art.

We claim:

1. A β-lactam compound of the formula

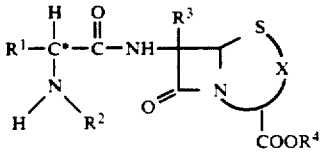

in which

X represents a radical of the formula

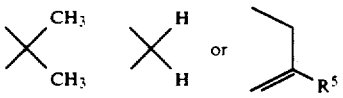

in which $R^5$ represents hydrogen, represents halogen, azido or represents straight-chain, branched or cyclic, alkyl which has up to 7 C atoms, *vinyl or propenyl* and which is optionally substituted by halogen, $C_1$–$C_5$-alkoxy, $C_{1-C5}$-alkylthio, —$OCONH_2$, $C_2$–$C_{10}$-acyloxy, by a pyridinium radical, or by a radical of the formula

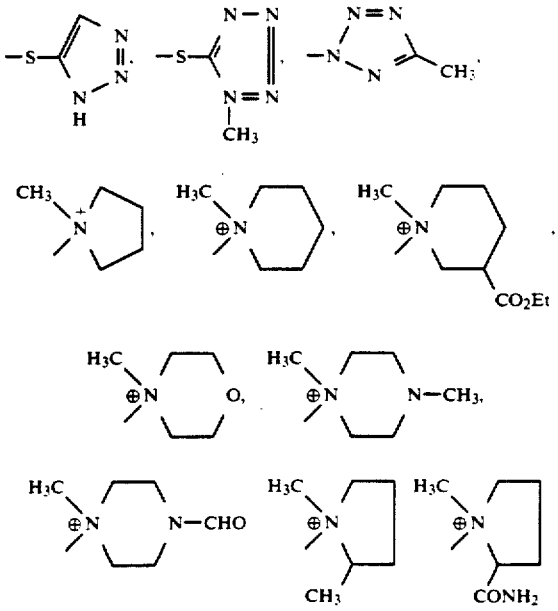

-continued

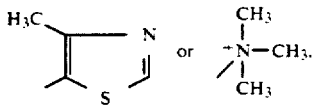

or represents alkoxy which has up to 5 C atoms or alkylthio which has up to 5 C atoms, $R^1$ represents the radical

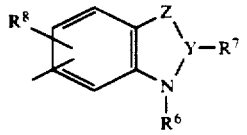

Y representing N or $CR^9$, or Y—$R^7$ representing C=O or C=N=$R^7$,

Z representing O, S or $NR^{10}$, $R^6$ representing hydrogen, representing hydroxyl or amino, or representing straight-chain, branched or cyclic, alkyl which has up to 10 C atoms and is optionally substituted by halogen, hydroxyl, cyano or $C_6$-$C_{10}$-aryl, $R^7$ representing hydrogen, representing straight-chain, branched or cyclic, alkyl which has up to 10 C atoms and which is optionally substituted by halogen, hydroxyl, alkoxy or alkoxycarbonyl, each having 1 to 6 C atoms, cyano, carboxyl, aryl, $SO_3H$ or by an amino group, or representing aryl, or $R^6$ and $R^7$ together completing a double bond, $R^8$ representing hydrogen, representing alkyl, alkoxy, alkylthio, each having 1 to 8 C atoms, representing trifluoromethyl or trifluoromethoxy, representing hydroxyl, mercapto, nitro or cyano, representing halogen, or representing an amino group, $R^9$ having the same meaning as $R^7$ and, additionally, representing halogen, representing $C_1$-$C_8$-alkoxy or $C_1$-$C_8$-alkylthio, representing an amino group, representing $SO_2$—$C_1$-$C_8$-alkyl or —$PO(OH)_2$, representing $SO_3H$ or $SO_2NH_2$, representing SH, OH, S-phenyl or O-phenyl, representing guanidino, amidino, —$NHNH_2$ or NHOH, representing pyrrolyl, pyrrolidinyl, pyrazolyl, imidazolyl, pyridyl, pyridazinyl, pyrimidyl, pyrazinyl, quinolyl, isoquinolyl, indolyl, quinoxalyl, quinazolyl, piperidinyl, morpholinyl, piperazinyl, thiomorpholinyl, furyl, thienyl, oxazolyl, thiazolyl, isoxazolyl, thiadiazolyl, triazolyl, S-pyridyl or O-pyridyl, $R^{10}$ having the same meaning as $R^6$ but not completing a double bond with $R^7$, or $R^9$ and $R^{10}$ together representing a $C_2$-$C_4$-methylene chain which is optionally interrupted by oxygen or sulphur, $R^2$ represents hydrogen or represents an amino-protective group, $R^3$ represents hydrogen, represents alkoxy or alkylthio, each having up to 5 C atoms, represents an amino group, or represents NHCHO, and $R^4$ represents hydrogen, represents a carboxyl protective group, represents —$CH_2$—O—CO—$C(CH_3)_3$, represents —$CH_2$—O—CO—$CH_3$ or —$CH(CH_3)$—O—CO—O—$C_2H_5$, represents the radical of the formula

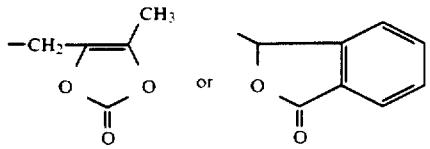

or represents alkali metal or ammonium ions.

2. A β-lactam compound according to claim 1, in which

X represents a radical of the formula

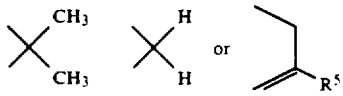

in which $R^5$ represents hydrogen, represents fluorine, chlorine or bromine, represents straight-chain or branched, alkyl which has up to 5 C atoms, *vinyl or propenyl* and which is optionally substituted by one or more of fluorine, chlorine, bromine, alkoxy having 1 to 3 C atoms, alkylthio having 1 to 3 C atoms, carbamoyloxy, acetyloxy, benzoyloxy or by a radical of the formula

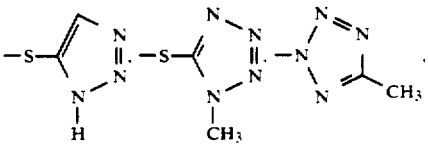

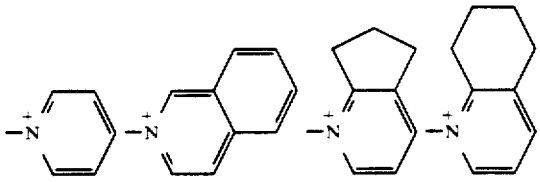

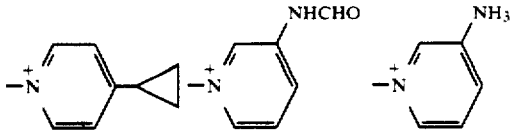

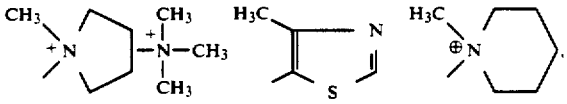

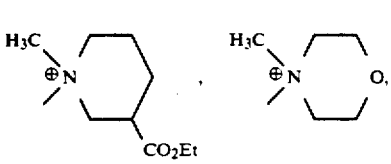

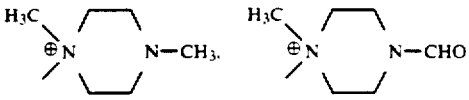

-continued

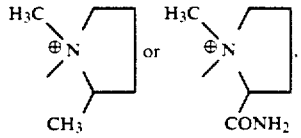

$R^1$ represents a radical of the formula

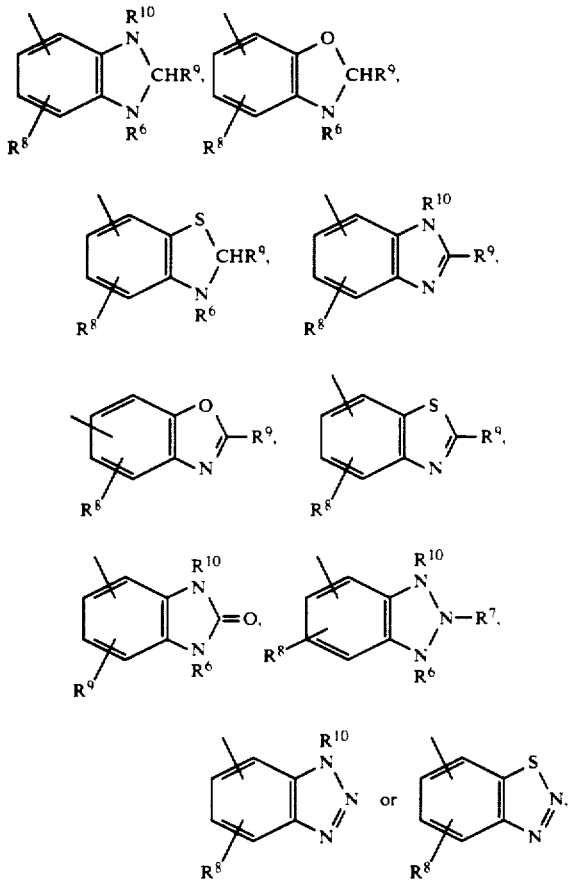

$R^6$ representing hydrogen, representing hydroxyl or amino, or representing straight-chain, branched or cyclic, alkyl which has up to 8 C atoms and which is optionally substituted by one or more fluorine, chlorine, bromine, optionally substituted amino, hydroxyl or phenyl, or representing aryl, $R^7$ representing hydrogen, or representing straight-chain, branched or cyclic, alkyl which has up to 8 C atoms and which is optionally substituted by one or more fluorine, chlorine, bromine, $C_1$-$C_4$-alkoxy, hydroxyl, carboxyl, phenyl, $SO_3H$ or an amino group, or representing aryl, $R^8$ representing hydrogen, representing alkyl, alkoxy or a alkylthio, each having 1 to 6 C atoms, representing trifluoromethyl or trifluoromethoxy, representing hydroxyl, mercapto, nitro or cyano, representing fluorine, chlorine or bromine, or representing an amino group, $R^9$ having the same meaning as $R^7$ and, additionally, representing fluorine, chlorine or bromine, representing $C_1$-$C_6$-alkoxy or $C_1$-$C_6$-alkylthio, representing an amino group, representing $—SO_2—C_1$-$C_6$-alkyl or $—PO(OH)_2$, representing $—SO_3H$ or $—SO_2NH_2$, representing SH, OH, S-phenyl or O-phenyl, representing guanidino, $—NHNH_2$ or —NHOH, representing pyrrolyl, pyrrolidinyl, pyrazolyl, imidazolyl, pyridyl, pyridazinyl, pyrimidyl, pyrazinyl, quinolyl, isoquinolyl, indolyl, quinoxalyl, quinazolyl, piperidinyl, morpholinyl, piperazinyl, thiomorpholinyl, furyl, thienyl, oxazolyl, thiazolyl, isoxazolyl, thiadiazolyl, triazolyl, S-pyridyl or O-pyridyl, $R^{10}$ having the same meaning as $R^6$ but not completing a double bond with $R^7$, or $R^9$ and $R^{10}$ together representing a $C_2$-$C_4$-methylene chain which is optionally interrupted by sulphur, $R^2$ represents hydrogen or represents an amino-protective group, $R^3$ represents hydrogen, represents alkoxy or alkylthio, each having 1 to 3 C atoms, represents an amino group, or represents NHCHO, and $R^4$ represents hydrogen, represents a carboxyl protective group, represents $—CH_2—O—CO—C(CH_3)_3$, represents $—CH(CH_3)—O—CO—O—C_2H_5$ or $—CH_2—O—CO—CH_3$, represents the radical of the formula

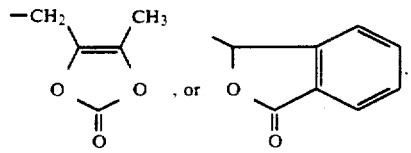

or represents $Na^+$, $Li^+$, $K^+$ or $NH_4^+$.

3. A β-lactam compound according to claim 1, wherein aryl represents phenyl which is substituted, identically or differently, once to three times by alkyl, alkylthio and alkoxy, each having 1 to 4 C atoms, halogen, nitro, cyano, hydroxyl, amino, trifluoromethyl, trifluoromethylthio or trifluoromethoxy.

4. A β-lactam compound according to claim 1, including an amino group of the formula

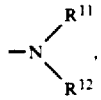

$R^{11}$ and $R^{12}$ being identical or different and representing hydrogen, representing aryl, representing $C_1$-$C_8$-alkyl, representing $C_7$-$C_{14}$-aralkyl, or representing $C_2$-$C_{10}$-acyl.

5. A β-lactam compound according to claim 1, wherein $R^2$ represents an amino-protective group selected from the group consisting of tert.-butoxycarbonyl, trityl, benzyloxycarbonyl, formyl, chloroacetyl and 1-methyl-2-ethoxycarbonylvinyl.

6. A β-lactam compound according to claim 1, wherein $R^4$ is a carboxyl-protective group selected from the group consisting of tert.butyl, decyl, 2,2,2-trichloroethyl, benzyl, 4-methoxybenzyl, 4-nitrobenzyl, triphenylmethyl, diphenylmethyl, acetoxymethyl, allyl and trimethylsilyl.

7. A β-lactam compound according to claim 1, wherein the heterocyclyl radical, when present is substituted once to three times, indentically or differently, by alkyl, alkylthio or alkoxy, each having 1 to 4 C atoms, halogen, nitro, cyano, hydroxyl, amino, trifluoromethyl, trifluoromethoxy or trifluoromethylthio.

8. A $\beta$-lactam according to claim 1, in which $R^5$ represents hydrogen, represents chlorine or fluorine, represents methyl, methoxy or methylthio, represents trifluoromethyl, vinyl, cis-propenyl, 3-chloro-1-propenyl, 3-iodo-1-propenyl, 3-pyridinio-1-propenyl, 3-(1-methyl-pyrrolidino)-1-propenyl, 3-(1H-1.2.3-triazol-5-yl)-thio-1-propenyl, 3-(4-methyl)-thiazol-5-yl)-1-propenyl or methoxymethyl, represents carbamoyloxymethyl, represents acetyloxymethyl or represents a radical of the formula

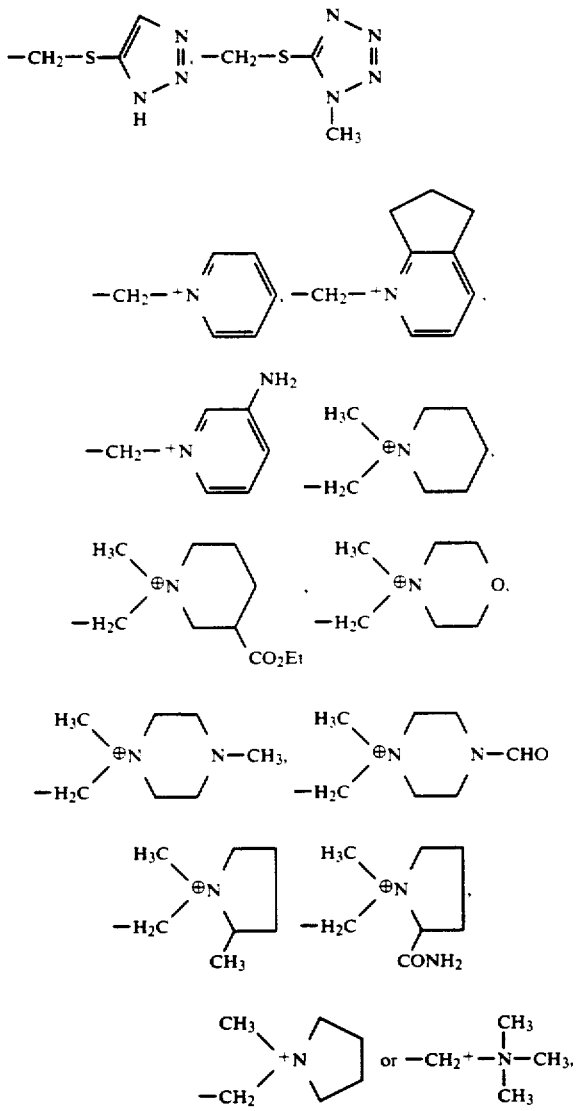

$R^1$ represents a radical of the formula

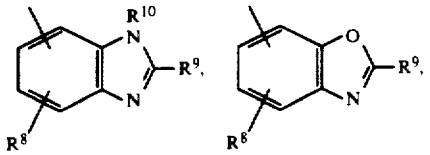

-continued

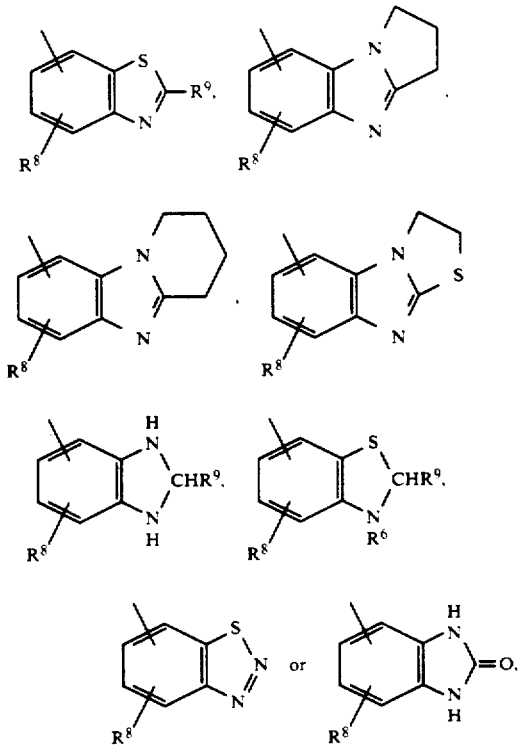

$R^6$ representing hydrogen, representing straight-chain, branched or cyclic, alkyl having up to 6 C atoms which is substituted by one or more of fluorine, amino, hydroxyl or phenyl, or representing aryl, $R^8$ representing hydrogen, representing alkyl, alkoxy or alkylthio, each having 1 to 4 C atoms, representing trifluoromethyl or trifluoromethoxy, representing hydroxyl, nitro or cyano, representing fluorine or chlorine, or representing amino, phenylamino, dimethylamino or acetylamino, $R^9$ representing hydrogen or representing straight-chain, branched or cyclic, alkyl which has up to 6 C atoms and which is optionally substituted by one or more of fluorine, chlorine, alkoxy having up to 2 C atoms, hydroxyl, carboxyl, phenyl, $SO_3H$, amino, $C_1$-$C_3$-alkylamino or dialkylamino, each of which has 1 to 3 C atoms, phenylamino, benzylamino or acetylamino, or representing fluorine, chlorine or bromine, representing $C_1$-$C_4$-alkoxy or $C_1$-$C_4$-alkylthio, representing aryl, representing amino, $C_1$-$C_3$-alkylamino or dialkylamino, each having 1 to 3 C atoms, phenylamino, benzylamino or acetylamino, representing $—SO_2—C_1$-$C_4$-alkyl, representing $SO_3H$ or $SO_2NH_2$, representing OH, SH, O-phenyl or S-phenyl, representing guanidino, $—NHNH_2$ or NHOH or representing pyrrolyl, pyrrolidinyl, pyrazolyl, imidazolyl, pyridyl, quinolyl, isoquinolyl, furyl, thienyl, morpholinyl, piperidinyl, piperazinyl or pyrimidyl, each of which can optionally be substituted by fluorine, chlorine, methyl, nitro, cyano, hydroxyl, trifluoromethyl, methoxy or amino, or representing S-pyridyl or O-pyridyl, $R^{10}$ having the same meaning as $R^6$, $R^2$ represents hydrogen, or represents an aminoprotective group, $R^3$ represents hydrogen, represents methoxy or methylthio, represents amino, $C_1$–$C_3$-alkylamino or dialkylamino, each having 1 to 3 C atoms, phenylamino, benzylamino or acetylamino or represents NHCHO, and $R^4$ represents hydrogen, represents a carboxyl protective group, represents $—CH_2—O—CO—C(CH_3)_3$, represents $—CH(CH_3)—O—CO—O—C_2H_5$, represents a radical of the formula

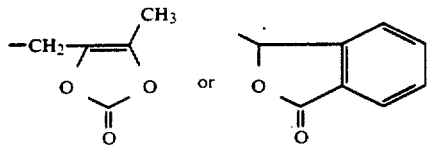

or represents $Li^+$, $Na^+$, $K^+$ or $NH_4^+$.

9. A β-lactam compound according to claim 1, wherein such compound is 7-(2-aminobenzothiazol-6-ylglycylamido)-3-chloro-3-cephem-4-carboxylic acid of the formula

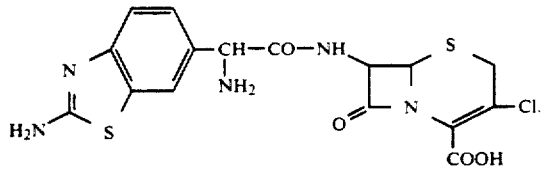

10. A β-lactam compound according to claim 1, wherein such compound is 7-(2-aminobenzothiazol-6-ylglycylamido)-3-methyl-3-cephem-4-carboxylic acid of the formula

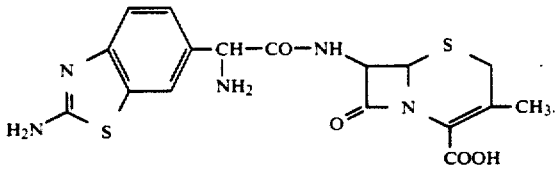

11. A β-lactam compound according to claim 1, wherein such compound is 6-(2-aminobenzothiazol-6-ylglycylamido)penicillanic acid of the formula

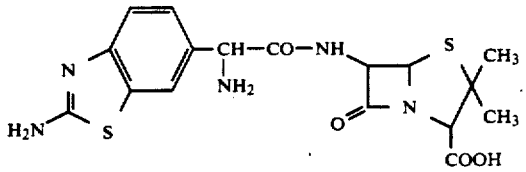

12. A β-lactam compound according to claim 1, wherein such compound is 7-(benzimidazol-5(6)-ylglycylamido)-3-chloro-3-cephem-4-carboxylic acid of the formula

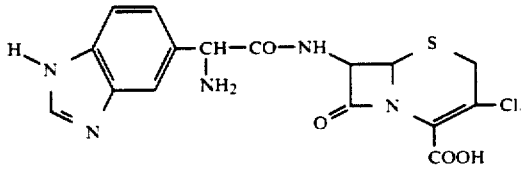

13. A β-lactam compound according to claim 1, wherein such compound is 7-(2-amino-1H-benzimidazol-5(6)-ylglycylamido)-3-chloro-3-cephem-4-carboxylic acid of the formula

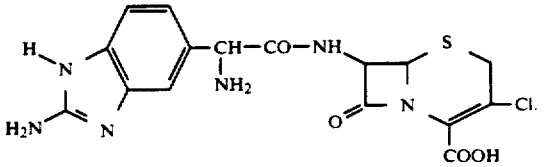

14. A β-lactam compound according to claim 1, wherein such compound is 7-(2-methyl-1H-benzimidazol-5-ylglycylamido)-3-chloro-3-cephem-4-carboxylic acid of the formula

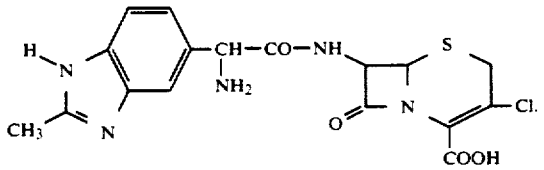

15. A β-lactam compound according to claim 1, wherein such compound is 7-(2-aminobenzoxazol-5-ylglycylamido)-3-chloro-3-cephem-4-carboxylic acid of the formula

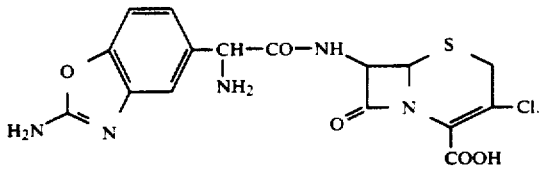

16. A β-lactam compound according to claim 1, wherein such compound is 7-(benzotriazol-5(6)-ylglycylamido)-3-chloro-3-cephem-4-carboxylic acid of the formula

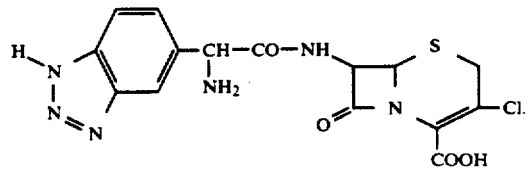

17. An antibacterial composition comprising an antibacterially effective amount of a β-lactam compound according to claim 1 in admixture with a pharmaceutically acceptable diluent.

18. A unit dose of a composition according to claim 17 in the form of a tablet, capsule or ampule.

19. A method of combating bacterial diseases in a patient which comprises administering to the patient in need thereof an antibacterially effective amount of a β-lactam compound according to claim 1.

20. The method according to claim 19, wherein such β-lactam compound is 7-(2-aminobenzothiazol-6-ylglycylamido)-3-chloro-3-cephem-4-carboxylic, 7-(2-aminobenzothiazol-6-ylglycylamido)-3-methyl-3-cephem-4-carboxylic, 6-(2-aminobenzothiazol-6-ylglycylamido)penicillanic acid, 7-(benzimidazol-5(6)-ylglycylamido)-3-chloro-3-cephem-4-carboxylic acid, 7-(2-amino-1H-benzimidazol-5(6)-ylglycylamido)-3-chloro-3-cephem-4-carboxylic acid, 7-(2-methyl-1H-benzimidazol-5-ylglycylamido)-3-chloro-3-cephem-4-carboxylic acid, 7-(2-aminobenzoxazol-5-ylglycylamido)-3-chloro-3-cephem-4-carboxylic acid or 7-(benzotriazol-5(6)-ylglycylamido)-3-chloro-3-cephem-4-carboxylic.

21. An animal feed or feed pre-mix comprising a growth promoting amount of a β-lactam compound according to claim 1 and an edible carrier.

22. A method of promoting the growth of an animal which comprises feeding said animal a growth promoting amount of a β-lactam compound according to claim 1.

23. A method according to claim 22, wherein such β-lactam compound is 7-(2-aminobenzothiazol-6-ylglycylamido)-3-chloro-3-cephem-4-carboxylic, 7-(2-aminobenzothiazol-6-ylglycylamido)-3-methyl-3-cephem-4-carboxylic, 6-(2-aminobenzothiazol-6-ylglycylamido)penicillanic acid, 7-(benzimidazol-5(6)-ylglycylamido)-3-chloro-3-cephem-4-carboxylic acid, 7-(2-amino-1H-benzimidazol-5-ylglycylamido)-3-chloro-3-cephem-4-carboxylic acid, 7-(2-methyl-1H-benzimidazol-5-ylglycylamido)-3-chloro-3-cephem-4-carboxylic acid, 7-(2-aminobenzoxazol-5-ylglycylamido)-3-chloro-3-cephem-4-carboxylic acid or 7-(benzotriazol-5(6)-ylglycylamido)-3-chloro-3-cephem-4-carboxylic.

* * * * *